United States Patent
Mahabadi et al.

(10) Patent No.: US 9,228,977 B2
(45) Date of Patent: Jan. 5, 2016

(54) CONTACTLESS CONDUCTIVITY DETECTOR

(75) Inventors: Kambiz Ansari Mahabadi, Singapore (SG); Isabel Rodriguez Fernandez, Singapore (SG); Chee Yen Lim, Singapore (SG); Jasmine Shu Ying Yuen, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 780 days.

(21) Appl. No.: 13/311,315

(22) Filed: Dec. 5, 2011

(65) Prior Publication Data

US 2012/0160691 A1 Jun. 28, 2012

Related U.S. Application Data

(63) Continuation-in-part of application No. 13/057,922, filed as application No. PCT/US2009/000277 on Aug. 7, 2009.

(60) Provisional application No. 61/087,000, filed on Aug. 7, 2008.

(51) Int. Cl.
*G01N 27/447* (2006.01)

(52) U.S. Cl.
CPC ...... *G01N 27/44791* (2013.01); *G01N 27/4473* (2013.01)

(58) Field of Classification Search
CPC .............. G01N 27/4473; G01N 27/44791
USPC ........................................... 324/603
See application file for complete search history.

(56) References Cited

U.S. PATENT DOCUMENTS

| 3,862,571 A | 1/1975 | Vogel |
| 3,901,079 A | 8/1975 | Vogel |
| 5,049,878 A | 9/1991 | Stern |
| 5,138,880 A | 8/1992 | Lee et al. |
| 5,455,418 A | 10/1995 | Hogan |

(Continued)

FOREIGN PATENT DOCUMENTS

| JP | 2009-244182 | 10/2009 |
| WO | WO00/16907 A1 | 3/2000 |

(Continued)

OTHER PUBLICATIONS

Laugere et al., Electronic baseline suppression for liquid conductivity detection ina capillary electrophoresis microchip, Proc. of IEEE, SEnsors, vol. 1, 2002, p. 450-453.*

(Continued)

*Primary Examiner* — Thomas F Valone
(74) *Attorney, Agent, or Firm* — Faegre Baker Daniels LLP

(57) ABSTRACT

A portable electrophoretic contactless conductivity detection ($C^4D$) system for analysis on a microfluidic chip houses in one embodiment a fluidic compartment for receiving the microfluidic chip, and four detection electrodes: first and second emitting electrodes, and first and second receiving electrodes. The first emitting electrode and the first receiving electrode are adjacent to a first channel wall of the microfluidic chip, and the second emitting electrode and the second receiving electrode are adjacent to a second channel wall, where the second channel wall is opposite to the first channel wall. In an embodiment, the electrodes are provided as portions of a removable cartridge cell.

25 Claims, 22 Drawing Sheets

(56) References Cited

U.S. PATENT DOCUMENTS

| | | |
|---|---|---|
| 6,748,804 B1 | 6/2004 | Lisec et al. |
| 6,823,731 B1 | 11/2004 | Lin |
| 9,007,075 B2 | 4/2015 | Mahabadi et al. |
| 2002/0031838 A1 | 3/2002 | Meinhart et al. |
| 2005/0109621 A1* | 5/2005 | Hauser et al. ............. 204/451 |
| 2009/0201035 A1* | 8/2009 | Kaltenbach et al. ......... 324/695 |
| 2009/0242754 A1 | 10/2009 | Kawaura |
| 2011/0140721 A1* | 6/2011 | Mahabadi et al. ............ 324/688 |
| 2012/0160691 A1 | 6/2012 | Mahabadi et al. |
| 2013/0172667 A1 | 7/2013 | Craig |

FOREIGN PATENT DOCUMENTS

| | | |
|---|---|---|
| WO | WO00/17630 A1 | 3/2000 |
| WO | WO00/75650 A1 | 12/2000 |
| WO | WO2005/033685 A2 | 4/2005 |

OTHER PUBLICATIONS

Zhang et al., Design of a movable contactless conductivity detector for microchip capillary electrophoresis, Nano/Micro Engineered and Molecular Systems, 2009. NEMS 2009. 4th IEEE International Conference on DOI: 10.1109/NEMS.2009.5068556 Publication Year: 2009 , pp. 190-193.*

Toth, A planar capacitive precision gauge for liquid-level and leckage detection, IEEE Trans. On Inst. And Meas., V. 46, No. 2, 1997, (pp. 644-646).

International Search Report for International Application No. PCT/SG2009/000277, issued by the Australian Patent Office on Oct. 27, 2009, (6 pgs.).

International Preliminary Report on Patentability for International Application No. PCT/SG2009/000277, issued by the Australian Patent Office on May 28, 2010, (9 pgs.).

* cited by examiner

CONTACTLESS CONDUCTIVITY DETECTOR

CROSS REFERENCE TO RELATED APPLICATIONS

This application is a Continuation-In-Part of co-pending U.S. Ser. No. 13/057,922, which claims priority to PCT/SG09/00277, filed on Aug. 7, 2009, which in turn claims the priority benefit to U.S. Provisional Application No. 61/087,000, filed on Aug. 7, 2008, all of which are incorporated herein by reference in their entireties.

FIELD OF THE INVENTION

The present invention relates to a device for analyzing and detecting analytes and more specifically to a new portable microfluidic analytical instrument based on electrophoresis as a separation technique and capacitive coupled contactless conductivity as a detector ($C^4D$). More particularly, it relates to a novel design of the $C^4D$ detection cell that allows for low background noise and low limit of detection (LOD). The portable system includes all the electronics and hardware components to do analysis of ionic species. The system is connected to a laptop computer for data acquisition and processing and is powered up by a battery for absolute autonomy.

BACKGROUND AND SUMMARY OF THE INVENTION

Lab-on-a-chip (LOC) based device requirements for analyte detection are sensitivity, universality and portability. To this date, these conditions have not been fully met and detection remains the main challenge in the development of LOC technology. Optical detectors, including fluorescence detection, have demonstrated the highest sensitivity. However, optical detectors are not universal and not easily made portable due to the size of the light sources. The use of electrochemical methods is well-suited for integration into portable systems, but they are less sensitive and prone to interferences. From the group of electrochemical sensors, $C^4D$ detectors are the most appealing as they fulfill the requirements of portability, universality for charged analytes and acceptable sensitivity.

The principle of $C^4D$ in combination with electrophoresis will now be described with reference to FIG. 1. FIG. 1 shows an arrangement of two external metal electrodes 100a, 100b in close proximity to an electrophoretic separation channel 102 in a microfluidic chip 104. The microfluidic chip 104 comprises two polymer sheets, namely top sheet 104a and bottom sheet 104b. The top sheet 104a provides access to reservoirs as will be described below, and the bottom sheet 104b provides the separation channel 102 that has been hot embossed into the bottom sheet 104b. In use, a run buffer reservoir 107, a first sample reservoir 109 and an outlet reservoir 111 of the microfluidic chip 104 are filled with electrophoretic run buffer solution, and a second sample reservoir 113 is filled with target analytes, typically ionic species dissolved in the run buffer solution. A separation voltage is then applied between the second sample reservoir 113 and the first sample reservoir 109. This drives 'plugs' of ions 114 into the separation channel 102. Subsequently, the separation voltage is applied between the run buffer reservoir 107 and the outlet reservoir 111 with all other reservoirs floating. This causes the plugs of ions 114 to be driven towards the electrodes 100a, 100b for detection.

The two external metal electrodes 100a, 100b and the electrophoretic separation channel 102 together form the $C^4D$ cell or detection cell. When the upstream/emitting electrode 100a emits an AC signal through the channel 102, it is capacitively captured by the downstream/receiving electrode 100b. The electrodes 100a, 100b are in the same plane and are attached to a top plate that seals the channel 102 and are typically placed in an anti-parallel configuration with respect to the length of the channel 102. The applied AC signal (typically 50-600 kHz) from the emitting electrode 100a capacitively couples through the channel 102 to the receiving electrode 100b, resulting in a small current that is amplified by an amplifier 106, rectified and offset-corrected using a rectifier 108, filtered and that undergoes data acquisition using a data acquisition tool (DAQ) 110 and finally recorded in a computing device 112 or other storage device as a DAQ graph.

The $C^4D$ cell can be considered as a combination capacitor-resistor-capacitor (CRC) electrical circuit, where the electrodes 100a, 100b and the channel's electric double layer form the capacitors, and the section of the channel 102 between the electrodes 100a, 100b forms the resistor. When a plug of ions 114 is driven through the section of the channel between the electrodes, the measured impedance of the system changes instantaneously because of the change in the resistance due to the different conductivity of the ionic species passing through the electrodes within the background electrolyte. In practical terms, this leads to a sudden change in the zero leveled output voltage or a peak in the DAQ graph. By electrophoresis, separated plugs of ions can be driven through the $C^4D$ cell at different times and the corresponding signal recorded, thus obtaining separated peaks according to the times at which the ions cross the $C^4D$ cell. Each peak is related by time to a specific ion, and the area under the peaks is related to the concentration of the specific ion. $C^4D$ in combination with electrophoresis therefore provides qualitative and quantitative analysis.

The capacitive coupled contactless conductivity detection ($C^4D$) cells reported to date use two electrodes placed externally over the separation channel. An example is illustrated in FIGS. 2(a) and (b), which respectively show a perspective view and plan view of a conventional detection cell. As noted earlier, electrodes 100a, 100b in conventional detectors are fixed to a top plate 200 that seals the separation channel 102 and are typically placed in an anti-parallel configuration with respect to the channel 102. In this configuration, the capacitance coupling to the solution in the channel 102 is inefficient and requires a high frequency and high voltage to couple the signal to detect low concentration samples. High frequencies, however, result in stray capacitance having a more significant effect. Changes in the conductivity of the solution will then only result in a small change over the background signal.

To reduce or eliminate the stray capacitance, different strategies have been employed such as placing a ground plane 202 between the electrodes 100a, 100b to shield their direct crosstalk (as shown in FIGS. 2(a) and (b)). However, while these strategies decrease the stray capacitance somewhat, the resulting detection sensitivity remains limited.

One alternative option to improve capacitance is to increase the magnitude of the AC voltage. However, high voltage levels are difficult to produce and are not safe to handle in portable systems. Another option to have increased capacitance is to use relatively large electrodes or detection lengths, but these approaches severely decrease resolution.

Without compromising resolution, one effective way to increase sensitivity in capacitive coupling detection is to reduce the distance between the electrodes at the detection area or the section of the channel between the electrodes (also known as the 'detection cell volume'). Known arrangements have achieved this by either: (i) scribing off some portion from the chip surface so that electrodes can be disposed nearer to the channel, or (ii) incorporating electrodes within the chip (integrated chip) during the microfabrication so that they are close enough to the channel. These approaches are either inaccurate (for option (i) above) or require complex fabrication processes (for option (ii) above).

To improve the portability of LOC devices, improvements have been made to releasbly attach the system to a laptop computer. The advantage of portable systems is that tests and analysis can be done onsite and when needed, which improves efficiency and decreases costs. In addition, transportation of the samples exposes the samples to conditions where the sample may possibly be contaminated or degraded. The portable system is user friendly and simple to operate. Therefore, it does not need highly trained personnel to operate the lab-on-a-chip analytical instrument. The system is also low cost and rugged to be carried and transported.

In the past decade, there have been efforts on developing portable instrumentation with somewhat limited success. In the area of electrophoresis, currently a few portable systems have been described where $C^4D$ is used as detector. One of them was developed for glass capillaries which typically require higher voltages to substantiate a high electric fields as the capillaries have longer length than microfluidic devices. This system is described in Electroanalysis 19, 2007, No. 19-20, pp. 2059-2065 by Kuban, P; Nguyen, H T A; Macka, M; Haddad, P R; Hauser, P C. Another system is from Innovative Sensor Technologies GmbH called TraceDec. This system uses glass microfluidic chips which are not disposable due to cost. The sensing electrodes are place at a far distance form the defection volume which results on low sensitivity. Another version that has been commercialized is described in IEEE SENSORS JOURNAL, VOL. 8, NO. 5, MAY 2008 by Holger Mühlberger, Wonhee Hwang, Andreas E. Guber, Volker Saile, and Werner Hoffmann. This system uses microchips with detection electrodes that are micro patterned on the outer surface of a plastic microfluidic chip. Due to this extra fabrication step, the cost of these types of chips increases drastically. Another $C^4D$ system is being commercialized by eDAQ Pty Ltd This system is modular, not fully integrated and involves the powers supply module, the C4D electronics module and the microfluidic C4D detection platform The electrophoresis microfluidic chip sits atop the $C^4D$ platform where the pair of electrodes for transmitting and receiving the AC signal are located only at the bottom plane. The electrodes are brought into contact with the chip from one side only and there is no ground plane between them to shield them from direct coupling to eliminate stray capacitance. The sensing electrodes are of fixed dimensions and not exchangeable. The cell is not encased into a housing to shield the whole cell from external interference effects or noises.

With the present invention, we developed a new generation of portable $E-dC^4D$ that provides improved sensitivity, low detection limit and at the same time it is low cost which reduces the price per analysis.

The present invention relates to the use of emitting electrodes positioned or positionable adjacent to and on opposite sides of a microfluidic channel, and receiving electrodes adjacent to and positioned or positionable on opposite sides of a microfluidic channel.

In one specific expression, the present invention relates to a contactless conductivity detection cell including: a microfluidic chip having a channel defined by channel walls, first and second emitting electrodes, and first and second receiving electrodes, wherein the first emitting electrode and the first receiving electrode are adjacent a first channel wall, and the second emitting electrode and the second receiving electrode are adjacent a second channel wall, the second channel wall being opposite the first channel wall.

Preferably the emitting electrodes and receiving electrodes are substantially planar and substantially parallel to each other.

Preferably the emitting electrodes are placed one on top and one at the bottom of the chip passing over the channel, and are configured to act as electrostatic image of each other to concentrate and focus signals from each other into a detection cell volume of the detection cell. Similarly, the receiving electrodes are preferably placed one on top and one at the bottom of the chip covering channel, and are configured to act as electrostatic images of each other to extract coupled signal from a detection cell volume of the detection cell.

Preferably the electrodes are each positioned at a distance of between 1 μm and 1000 μm from the channel and preferably the microfluidic chip has a thickness in the range of 30 μm to 1 mm.

Preferably the detection cell further comprises a first ground plane between the emitting electrodes and the receiving electrodes, and a grounded metal housing containing the emitting electrodes, the receiving electrodes and the first ground plane.

Preferably the detection cell further comprises a second ground plane configured to shield the emitting electrodes and the receiving electrodes from interferences from electronic components housed in the grounded metal housing while keeping a very close distance between the receiving electrodes and the receiving amplifier encased in a second shielded housing.

Preferably at least part of the channel between the emitting electrodes and the receiving electrodes has a restricted submicron-sized or nano-sized width/cross-section.

In one form, the first emitting electrode and the first receiving electrode are preferably arranged on or in a top plate of the microfluidic chip, and where the second emitting electrode and the second receiving electrode are adjacent a base of the channel. In another form, the first emitting electrode and the first receiving electrode are preferably arranged adjacent one side of the channel, and wherein the second emitting electrode and the second receiving electrode are arranged adjacent an opposite side of the channel.

Preferably the detection cell further comprises multiple parallel channels, each channel having a pair of emitting electrodes and a pair of receiving electrodes, wherein all of the emitting electrode pairs are connected to a single input.

In another expression, the present invention relates to a portable electrophoretic micro fluidic system and a contactless conductivity detection system comprising: a platform having an opening configured to receive a microfluidic chip having a channel defined by channel walls, a cover configured to close at least part of the opening, first and second emitting electrodes, and first and second receiving electrodes, wherein the first emitting electrode and the first receiving electrode are configured to be positioned adjacent a first channel wall, and the second emitting electrode and the second receiving electrode are configured to be positioned adjacent a second channel wall, the second channel wall being opposite the first channel wall.

Preferably the system is battery powered, which allows for greater portability.

Preferably the cover is configured to secure at least part of a microfluidic chip between the cover and the base of the opening.

Preferably the second emitting electrode and the second receiving electrode are positioned on or adjacent the base of the opening.

Preferably the first emitting electrode and the first receiving electrode are positioned on or adjacent an internal surface of the cover. Preferably the cover includes a holder on the internal surface, and wherein the first emitting electrode and the first receiving electrode are positioned on the holder.

Preferably the holder is resiliently coupled to the cover and is configured to press the first emitting electrode and the first receiving electrode against a microfluidic chip.

Preferably the detection system further comprises one or more slots to allow a microfluidic chip to be inserted into the opening.

Preferably the cover is selected from a group consisting of: a pivotable cover and a detachable cover.

Preferably the emitting electrodes and/or the receiving electrodes are movable along the channel.

Preferably the opening is configured to allow a microfluidic chip to be movable within the opening.

Preferably the detection system further comprises a current-to-voltage converter adjacent and connected to the receiving electrodes, and a rectifier, low-pass filter, and offset circuit connected to the current-to-voltage converter. Preferably the detection system further comprises an alternating current function generator adjacent and connected to the emitting electrodes, and a miniaturized high voltage power supply. Preferably the detection system further comprises detection electronics arranged on a circuit that comprises a top layer and a bottom layer, the top layer being isolated from the bottom layer.

In yet another specific expression, the present invention relates to a capacitive coupled contactless conductivity detection cell comprising: a microfluidic chip having a channel, and detection electrodes placed in a top-bottom geometry and in close proximity to the channel.

In still another specific embodiment, the present invention relates to a capacitive coupled contactless conductivity detection cell including: detection electrodes placed in a top-bottom geometry in a housing, a detection area located within the housing, a Faraday shield, and a grounded metal housing, wherein the electrodes are shielded from direct cross talk or external noise by the Faraday shield and the grounded metal housing.

Preferably the detection electrodes comprise two emitting electrodes and two receiving electrodes.

Preferably the emitting electrodes are placed one on top and one at the bottom of the channel, and are configured to act as electrostatic images of each other to concentrate and focus the signals from each other into a detection cell volume of the detection cell.

Preferably the receiving electrodes are placed one on top and one at the bottom of the channel, and are configured to act as electrostatic images of each other to extract coupled signals from a detection cell volume of the detection cell.

Preferably the detection electrodes comprise two emitting electrodes and two receiving electrodes separated by the Faraday shield and located in the grounded metal housing.

Preferably the housing holds a microfluidic chip inserted into a holder within the emitting and receiving electrodes.

Preferably the emitting and receiving electrodes are placed close to the separation channel, and are movable by a cover to adjust a detection cell volume of the detection cell.

Preferably the detection area is adjustable by moving the microfluidic chip within the emitting and receiving electrodes.

In one form of the invention the electrodes are provided within a replaceable cartridge cell. In use the cartridge cell is intended to sandwich the detection cell with the microfluidic channel. The cell may be releasably attached to the rest of the detecting system by a mechanism which electrically connects the emitting electrodes and the receiving electrodes to corresponding electrical contacts of the housing. A variety of replaceable cartridges may be provided, suitable respectively for different applications in terms of detection sensitivity and resolution. For example, they may differ in their electrode dimensions and gap distance. Thus, in contrast to embodiments in which these parameters are variable, this form of the invention is robust, and less complex, which reduces cost. A user can adapt the measurement which is made very easily by replacing one cartridge with another.

The present invention provides a $C^4D$ cell with improved sensitivity and detection limit compared to detection cells of the state of the art. A benefit of improving sensitivity is that the present invention can be implemented using lower power inputs than previously employed. The gap distance between the detection electrodes is made adjustable in accordance with certain embodiments of the invention, hence the detection cell length and thus the limit of detection (LOD, which determines sensitivity) and/or peak separation (which determines resolution) can be fine-tuned depending on demands of the specific application Where a shielded housing is provided containing all the necessary electronics and the $C^4D$ cell, an enhanced signal-to-noise ratio (S/N) is able to be obtained, which results in a highly sensitive portable electrophoretic analyzer. Embodiments of the present invention also provide a $C^4D$ detection device that has low power requirements. These and other related advantages will be readily apparent to skilled persons from the description below.

BRIEF DESCRIPTION OF THE FIGURES

Non-limiting embodiments of the present invention will now be described by way of example with reference to the accompanying figures in which:

FIG. 22(a)-(c) illustrates the replaceable dC$^4$D cartridges showing the top-bottom excitation and pickup electrodes with a ground plane in between.

FIG. 25 (b) is a schematic diagram of the pin self-latching mechanism to contact the cell to input output signals and ground.

DETAILED DESCRIPTION OF THE PREFERRED EMBODIMENTS

First Set of Embodiments

Figure 3:
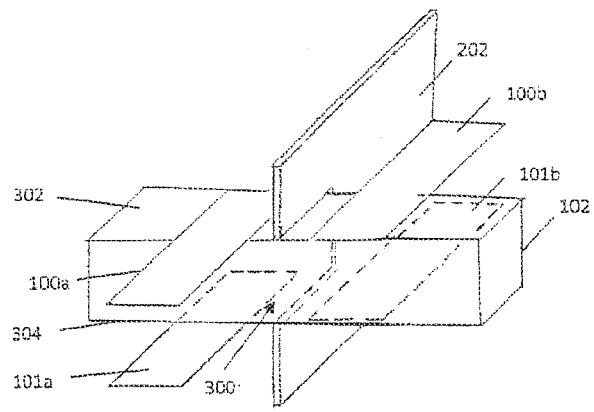
FIG. 3 is a diagram of the $C^4D$ detection cell electrode arrangement of the present invention.

Referring to FIG. 3, the present invention in one preferred embodiment comprises a capacitively-coupled contactless conductivity detector comprising a microfluidic electrophoretic chip (not shown) having a separation channel 102 thereon, first and second emitting electrodes 100a, 101a, and first and second receiving electrodes 100b, 101b on the chip and adjacent the separation channel 102. Between the emitting electrodes 100a, 101a and the receiving electrodes 100b, 101b is a detection area generally indicated with arrow 300. As will be described in detail below, the first and second emitting electrodes 100a, 101a are configured to concentrate signals emitted from one another to the detection area 300, and the first and second receiving electrodes 100b, 101b are configured to extract signals from the detection area 300.

FIG. 3 shows that the separation channel 102 is defined by channel walls, with the first emitting electrode 100a and the first receiving electrode 100b being located adjacent a first channel wall 302. The first channel wall 302 forms part of the top plate of the microfluidic chip. The second emitting electrode 101a and the second receiving electrode 101b are located adjacent a second channel wall 304, which is opposite the first channel wall 302. This allows for maximum concentration and extraction of signals within the detection area 300. The receiving electrodes 100b, 101b are displaced along the length of the channel 102 from the emitting electrodes 100a, 101a, with the area in the channel 102 between the emitting and receiving electrodes defining the detection area 300. The second channel wall 304 forms part of the base of the channel 102 in the preferred embodiment. For ease of reference, this arrangement or geometry of electrodes will herein be referred to as a top-bottom geometry. Accordingly, the first emitting electrode 100a is a top emitting electrode, the second emitting electrode 101a is a bottom emitting electrode, the first receiving electrode 100b is a top receiving electrode and the second receiving electrode 101b is the bottom receiving electrode. Also for ease of reference, the emitting and receiving electrodes will collectively be referred to as detection electrodes.

All of the detection electrodes 100a, 100b, 101a, 101b are substantially planar, parallel to each other, and are arranged in close proximity to the detection area 300 to enhance the coupling of the excitation signals into the channel 102 and to prevent loss of signals to be extracted. The distance between the detection electrodes and the channel is preferably between 75 μm-150 μm. This is, however, a non-limiting range as the distance may be set anywhere from 1 μm-1000 μm depending on a variety of factors (e.g. chip thickness, method of electrode placement, application desired etc). To avoid direct coupling or crosstalk between the emitting and receiving electrodes, a ground plane 202 is provided.

The separation channel 102 of the preferred embodiment is fabricated in a thin plastic (e.g. 30 μm-1 mm, a non-limiting example being a 125 μm polymeric) or glass film with the detection electrodes being disposed (e.g. by sputtering) on hot embossed sealed channels on the film that are arranged to allow positioning of the detection electrodes near the detection cell volume. The use of thin microfluidic chips allows the placing of the detection electrodes in close proximity to the channel so as to achieve a large capacitance, and thus, a larger signal output. It is, however, not essential that the detection electrodes be printed on the microfluidic chip itself. An alternative placement of the detection electrodes will be described in further detail with reference to the portable detector embodiment in FIG. 13.

Figure 4:
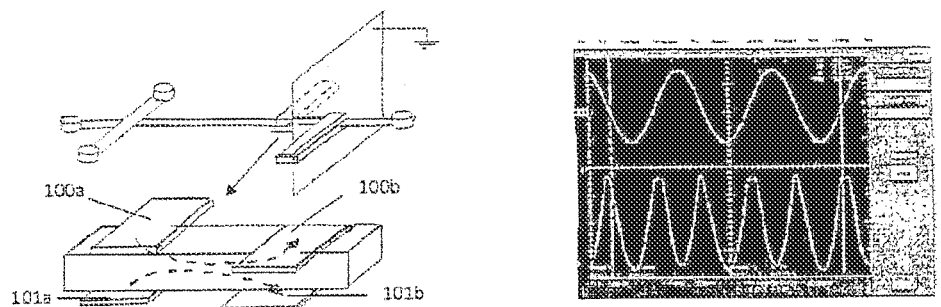
FIG. 4 is a diagram of the electrode arrangement of the present invention and the output signals from the electrode arrangement of the present invention.
Figure 5:
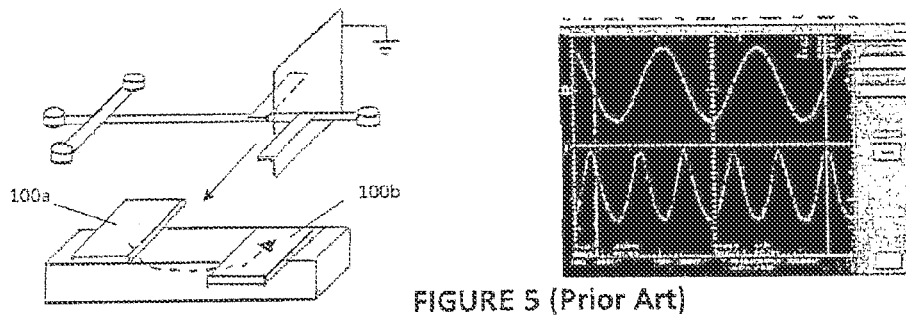
FIG. 5 is a diagram of a conventional electrode arrangement and the output signals from the conventional electrode arrangement.

As will be appreciated from FIGS. 4 and 5, the electrode arrangement above improves the coupling and extraction of the signals through the detection cell volume, resulting in a more precise and sensitive analysis capability. Specifically, the figures show a comparison of the output signals captured by an oscillator between the cell geometry of the preferred embodiment (FIG. 4) and that of a conventional detection cell (FIG. 5). Given an input signal of 300 kHz, 50 $V_{pp}$, the amplitude of the output signal of the preferred embodiment is at 600 kHz, 0.62 $V_{pp}$. A similar input to the conventional electrode arrangement (with the same electrode dimensions and the same detection volume) also produces an output of 600 kHz but at only 0.46 $V_{pp}$.

The voltage amplitude increase in the output signal in the present invention is the result of a better coupling between the electrodes placed in the configuration of the present invention. One reason for this is that both the top and bottom emitting electrodes 100a, 101a are connected to one source of excitation signal, which causes the emitted signal from the top electrode 100a to be repelled and concentrated into the detection area of the channel 102 by the bottom electrode 101a and vice versa. In other words, the electrodes 100a, 101 form a quasi closed conductor (acting as electrostatic images of each other) reflecting the electrical signals into the detection cell volume, thus concentrating and increasing the electric field lines in the detection cell volume. Also, at the receiving electrodes 100b, 101b, the chances of losing signals are reduced as both electrodes 100b and 101b are there to collect the incoming signals. As a result of the increased number of electric field lines in the detection cell volume and the reduced loss of signals to be extracted, improved signal interaction and signal extraction are made possible from every charge passing through the detection cell volume.

It should be noted that the detection cell length determines the signal output. Increasing the detection length by increasing the displacement or separation gap between the electrodes will increase the signal intensity. However, at the same time, it will also reduce resolution or the ability to discern between two separated plugs, which is important in order to identify and quantify analytes of interest. Depending on the particular application, these two parameters (signal intensity vs. resolution) will need to be optimized simultaneously and balanced. In the preferred embodiment, therefore, the displacement between the emitting and receiving electrodes is adjustable by having at least one pair movable along the separation channel. This allows adjustment of the detection limit (efficiency) and/or peak separation (resolution) depending on the demands of the specific application.

A series of experimental analysis were carried out to demonstrate the improvement in the output signal comparing conventional cell geometry and the cell geometry of the present invention. During the experiments, other conditions were kept exactly the same: input signal (sine wave 300 kHz, $50V_{pp}$), detection length (2 mm), electrode width (1 mm), buffer solutions and samples' concentration. A sample containing four cations at 0.05 mM concentration was analyzed by electrophoresis and the resulting signals were recorded in an electropherogram using a DAQ system. The following were the electrophoretic separation conditions: separation buffer, 10 mM His/tris buffer solution; L injection protocol by applying potential of 4 kV between the first and second sample reservoirs for 2 s, computer controlled switching to run buffer reservoir and the grounded outlet reservoir using 4 kV for separation; sample 0.05 mM cations ($NH_4^+$, $K^+$, $Na^+$, $Li^+$).

Figure 6:
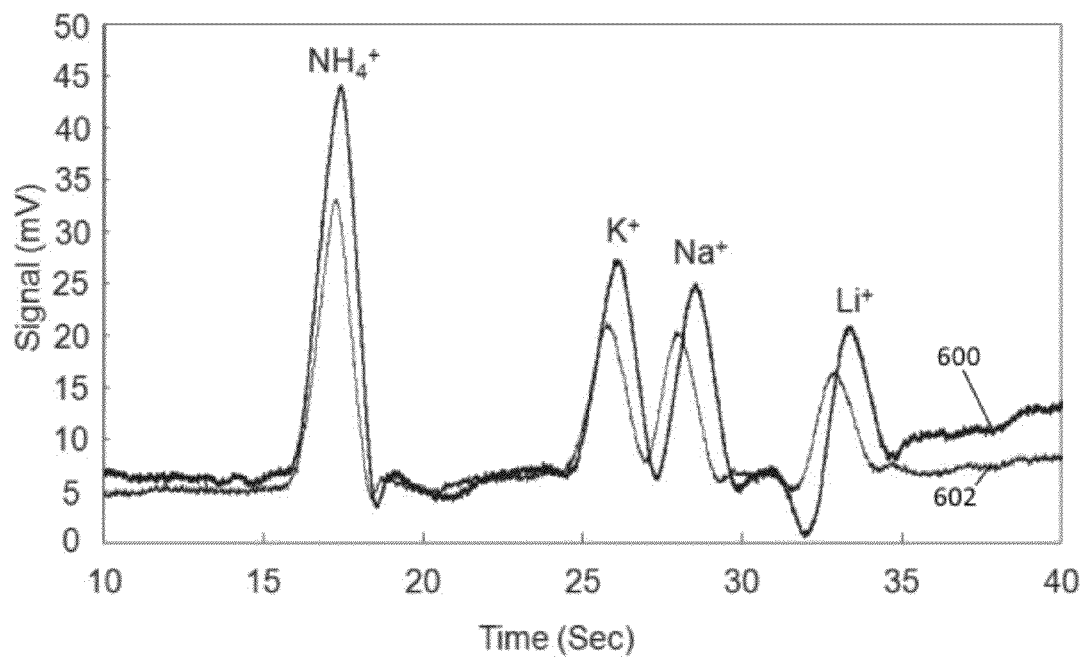
FIG. 6 is a graph comparing the signal intensity obtained using the electrode configuration of the present invention and using a conventional electrode configuration.

FIG. 6 shows the comparison between the electropherogram obtained from the top-bottom configuration of the preferred form (line 600) and the conventional configuration (line 602). The experimental results indicate an average of 20% increase in the peak height or approximately 0.2V increase for every volt of the output signal. For example, for the peak height of $K^+$ at 50 μm concentration, the signal is increased from 20 mV to 28 mV. This means that the ratio concentration/signal has been decreased from 2.5 Km/mV to 1.7 Km/mV. This accordingly improves the detection limit (i.e. a lower concentration of a sample is now sufficient to produce a discernable output).

In addition to providing a top-bottom configuration, embodiments of the present invention also provide additional improvements to $C^4D$ cell geometries.

Figure 7:
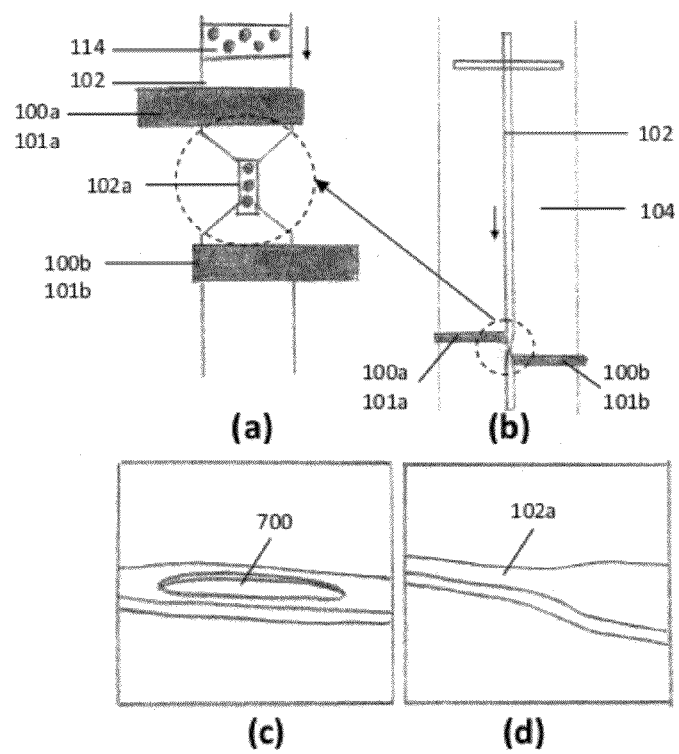
FIGS. 7(a) and (b) are schematics of a restricted-$C^4D$ detection cell configuration.
FIGS. 7(c) and (d) are schematics of the geometry of the molds used for hot embossing the restricted detection cell.

Referring to FIGS. 7(a) and (b), a chip 104 is shown with a separation channel 102, a plug of ions 114 and pairs of detection electrodes 100a, 101a and 100b, 101b. The detection electrodes are shown adjacent the detection cell volume of the separation channel 102, with at least part of the detection cell volume being scaled down to submicron and/or nanosize with a restrictive or narrowed-down channel 102a cross-section/width at or about the detection area. The restrictive channel 102a not only functions to increase resistance but also functions to enlarge the change of resistance from background to analyte. A higher change of resistance over the background signal translates to a higher output signal level i.e. the S/N ratio. The restrictive channel 102a may be fabricated using the molds shown in FIG. 7(c) or (d), which respectively provide two peripheral restrictions (i.e. around an obstruction 700 in the centre of the channel 102) and a central restriction to the channel 102.

Figure 8:
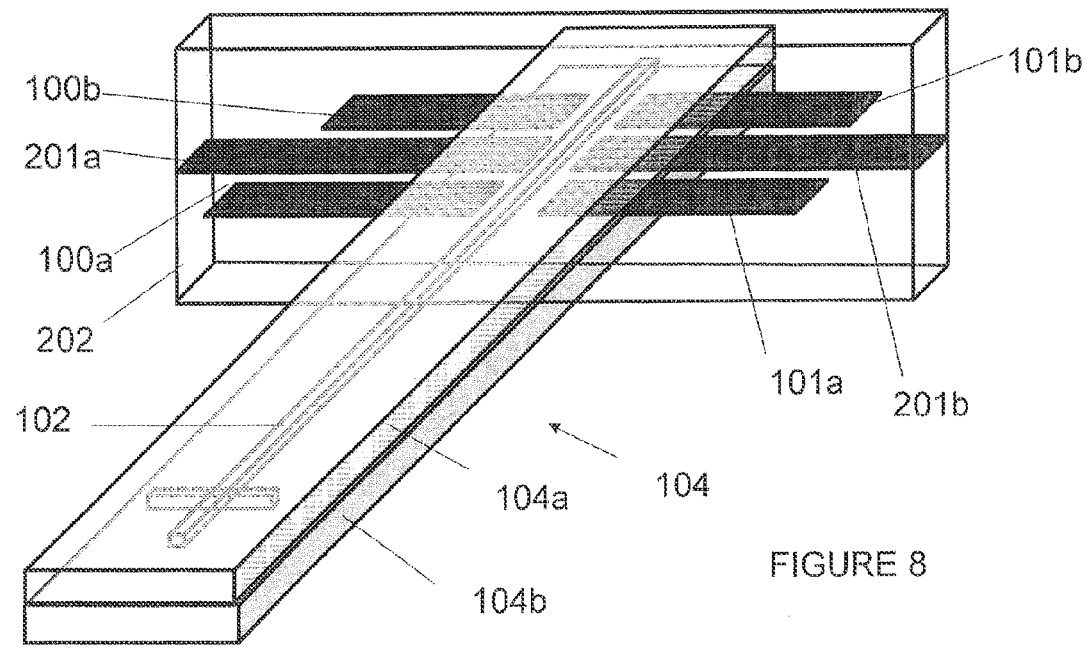
FIG. 8 is a schematic of a further embodiment of the electrode arrangement of the present invention.

In another embodiment, as shown in FIG. 8, the detection cell of the present invention comprises emitting electrodes 100a, 101a, ground shields 201a, 201b and receiving electrodes 100b, 101b that have been integrated into the chip 104 using thermal bonding. The ground shields 201a, 201b in addition to the plane ground shield 202 help to reduce further the stray capacitance due to coupling through the bulk polymer material between the emitting electrodes 100a, 101a, and receiving electrodes 100b, 101b. Each pair of electrodes is positioned laterally in parallel (i.e. the pairs are parallel in the same plane), in close proximity to the channel 102 and are bonded at the same time the channel and top cover of the chip are bonded. In another approach, the electrodes can be bonded between the plastic sheets (top sheet 104a and bottom sheet 104b) that form the chip 104 before the assembly is aligned and bonded to another piece of polymer sheet. A lateral hot embossed groove may be provided to facilitate the alignment before bonding. In this embodiment, the top electrodes are essentially on one side of the channel, and the bottom electrodes are on an opposite side.

Figure 9:
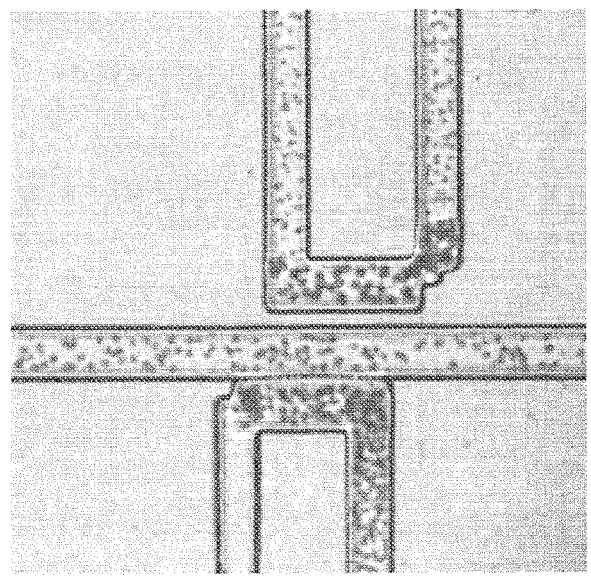
FIG. 9 is an image of electrodes of the present invention formed by hot embossing together with the cross channel prior filling with conductive material.

FIG. 9 shows a modification to the lateral electrode embodiment. In this modification, each lateral pair is in the form of enclosed lateral channels which are in close proximity to the separation channel 102 and which are filled with conductive material (although only one pair is shown in FIG. 9). In particular, the electrodes begin as channels hot embossed into the chip at the same time as when the cross channel is hot embossed, and then sealed. The design and the gap to the channel are tailored using the mold, hot embossing process and bonding conditions. Once the channels are formed and sealed, the channels are connected to reservoirs and are filled via pumps with a conductive material (e.g. silver paint) which, after drying, become conductive electrodes. The closest gap between the electrodes and the channel achieved in this configuration is 5 μm. By optimizing the hot embossing and boding conditions, the gap can be scaled down to even smaller sizes (e.g. 1 μm).

Figure 10:
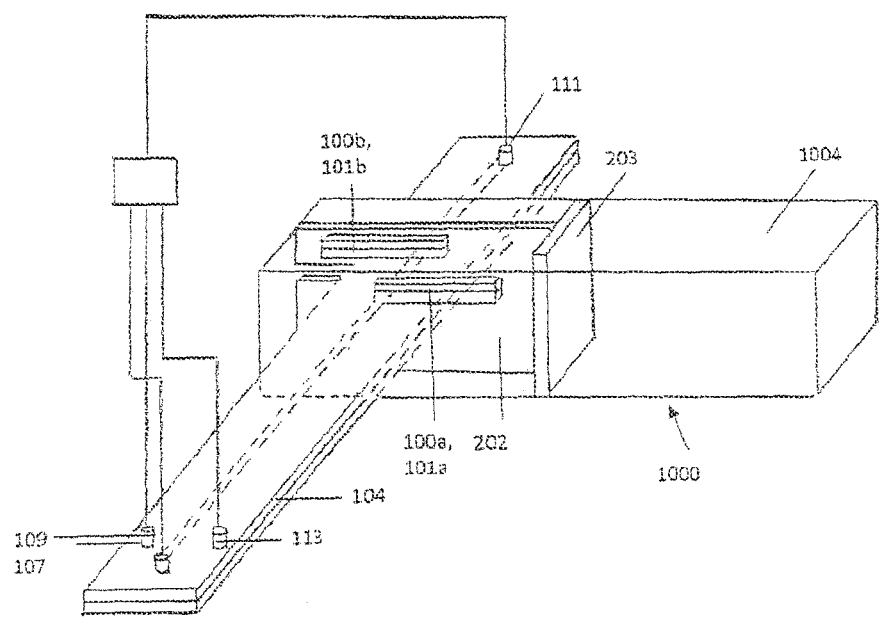
FIG. 10 is a schematic showing a $C^4D$ shielded housing.

In addition to a cell electrode geometry, the present invention also comprises a shielded housing for the $C^4D$ detector of the electrophoretic system. A schematic of one shielded housing of the detection cell is shown in FIG. 10. The housing 1000 acts as a Faraday shield to shield only the detection cell within the separation channel 102, leaving the rest of the microfluidic chip 104 accessible for input of fluids and application of high voltage for electrophoresis separation. The housing 1000 substantially eliminates interferences from external noise sources, from the DC power applied at the terminus of the channels, and from handling operations, such as sample and reagent injection etc. Specifically, a first ground plane 202 is provided to eliminate direct coupling between the detection electrodes, and a second ground plane 203 is provided to isolate the detection electronics from the $C^4D$ electrodes. In the embodiment illustrated, the first and second ground planes 202, 203 are in an anti-parallel (i.e. perpendicular) configuration with respect to each other.

The shielded housing 1000, which is made of metal and which preferably extends perpendicularly to the length of the chip 104, is grounded and includes a cavity 1004 in which the detection electronics and circuit is positioned. The detection electronics are arranged on a circuit that comprises two layers, i.e. top and bottom printed circuit board (PCB) layers. The top layer is isolated from the bottom layer and comprises an operational amplifier and exchangeable feedback resistor to convert current to voltage. A very short coaxial cable transfers the signal from the receiving electrodes through a hole to the top layer. Then, the converted voltage signal is transferred to the bottom layer for rectification, low pass filtering, and offset/gain baseline suppression to bring the level of the output signal to zero.

Figure 11A:
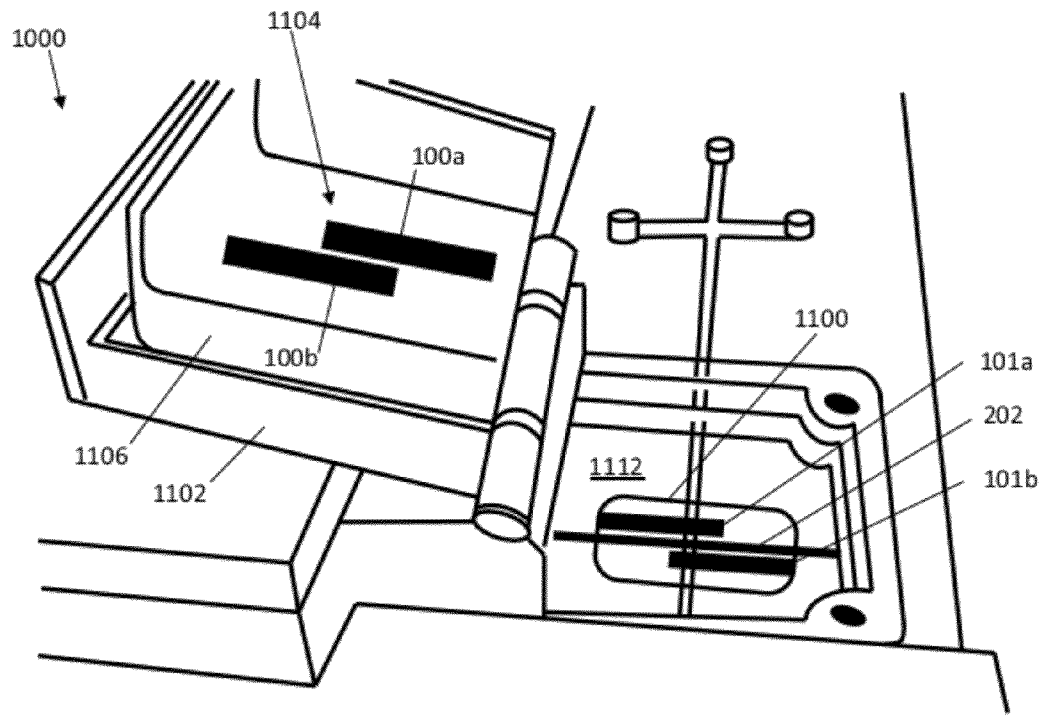
FIG. 11(a) is a schematic of C$^4$D housing showing the top and bottom electrodes disposed on a retractable electrode mechanism.

An alternative shielded housing 1000 is shown in FIG. 11A. As before, the housing 1000 includes top electrodes 100a, 100b and bottom electrodes 101a and 101b together with a ground plane 202. A Faraday shield 1100 is provided to shield the detection electrodes and the detection area between the electrodes. The shielded housing of FIG. 11A further includes a pivotable cover 1102 to allow access to the detection cell. In one embodiment, the cover 1102 includes a retractable electrode mechanism 1104, which is configured to sandwich a microfluidic chip in the housing 1000 and to press the detection electrodes against the chip tightly when the cover 1102 is closed so as to achieve closest proximity and to avoid air gaps between the detection electrodes and the separation channel.

Figure 11B:
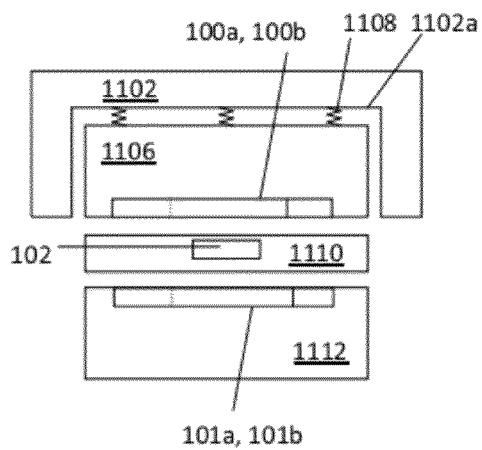
FIG. 11(b) is a cross-section view of the housing of FIG. 11(a) with a microfluidic chip.

The retractable electrode mechanism 1104 of the preferred embodiment includes a holder 1106 that is resiliently coupled to the internal surface 1102a of the cover 1102 and that secures the top emitting and receiving electrodes 100a, 100b. The resilient coupling is by way of springs 1108 as shown in FIG. 11B. FIG. 11B also shows the placement of a microfluidic chip 1110 having a channel 102 in the opening between the cover 1102 and the base 1112 of the opening of the device in or on which the bottom electrodes 101a, 101b are located. The cover 1102, chip 1110 and base 1112 are shown in FIG. 11B having gaps therebetween for clarity. In use, gaps in the arrangement are minimized by having the cover 1102 clamp down so as to press and secure the chip 1110 on the base 1112.

Figure 11C:
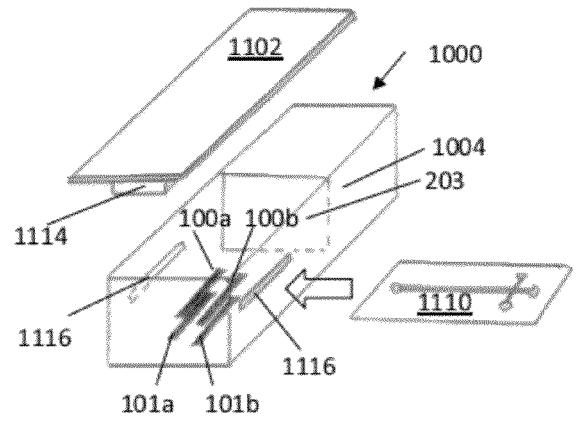
FIG. 11(c) is an alternative embodiment of the shielded housing.

Another alternative embodiment of the shielded housing 1000 is shown in FIG. 11C. The housing 1000 in this embodiment is similar to that of FIG. 10 but includes a detachable cover 1102. The cover 1102 is arranged to press against a resilient spacer 1114, which in turn presses the top electrodes 100a, 100b against the microfluidic chip 1110. This in turn presses against the bottom electrodes 101a, 101b, thus optimizing the proximity of the detection electrodes to the detection area. In this configuration, the chip 1110 is slid into position via slots 1116 in the housing 1000. The top and bottom electrodes 100a, 100b, 101a, 101b are positioned such that when the chip 1110 is slid into position, the top electrodes 100a, 100b are automatically positioned on one side of the chip 1110, while the bottom electrodes 101a, 101b are automatically positioned on the opposite side of the chip 1110.

In the arrangement of the housing 1000 of FIG. 11C, the chip 1110 is placed as close as possible to the electronics in the housing 1000. The housing therefore includes a cavity or compartment 1004 to contain the electronic components of the device, like the embodiment of FIG. 10. A first ground shield (not shown) is arranged between the emitting and receiving electrodes while a second ground shield 203 is arranged to separate the detection cell from the electronic components. This arrangement allows minimal signal losses and interference from noise signals from outside the detection cell.

Figures 12A, 12B:
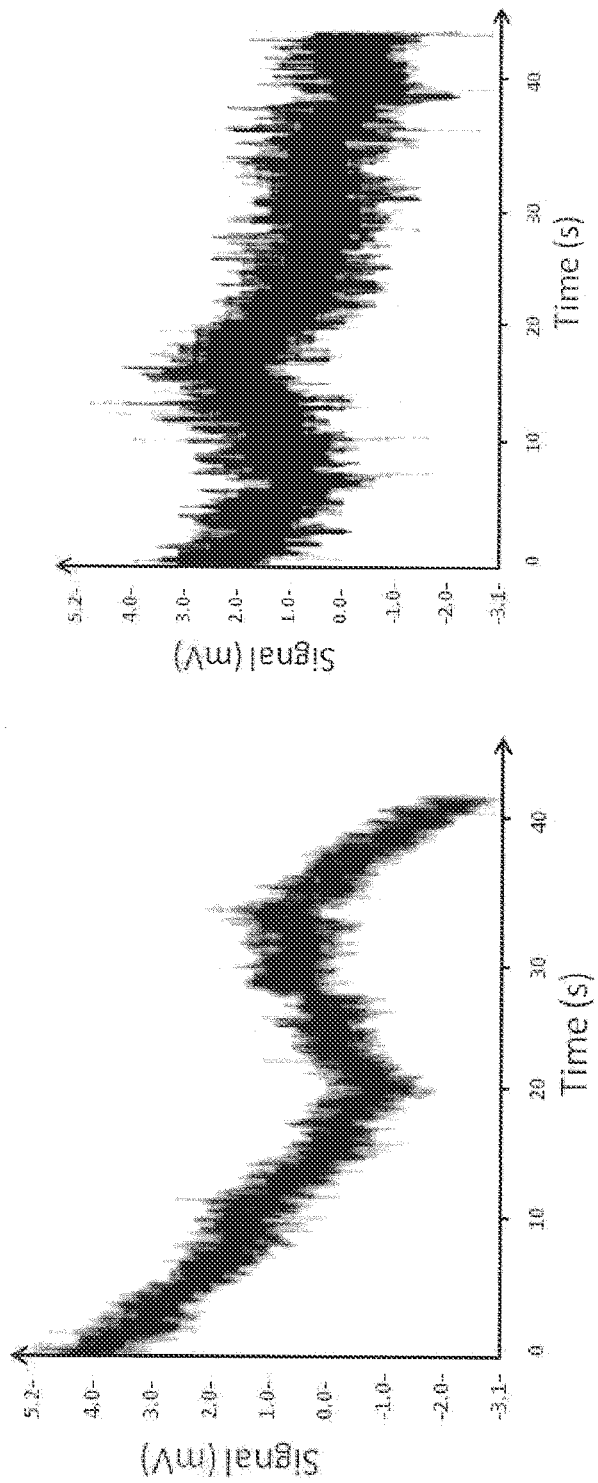
FIGS. 12(a) and (b) are graphs respectively showing noise level before using the shielded housing and after using the shielded housing.

FIGS. 12(a) and (b) respectively show a comparison of the noise level without and with the shielded housing. Without using the shielded housing, the level of noise for a signal of 300 kHz, $20V_{pp}$ is between 3 to 4 mV, while with the shielded housing, this value is reduced to 1 to 2 mV.

Figure 13:
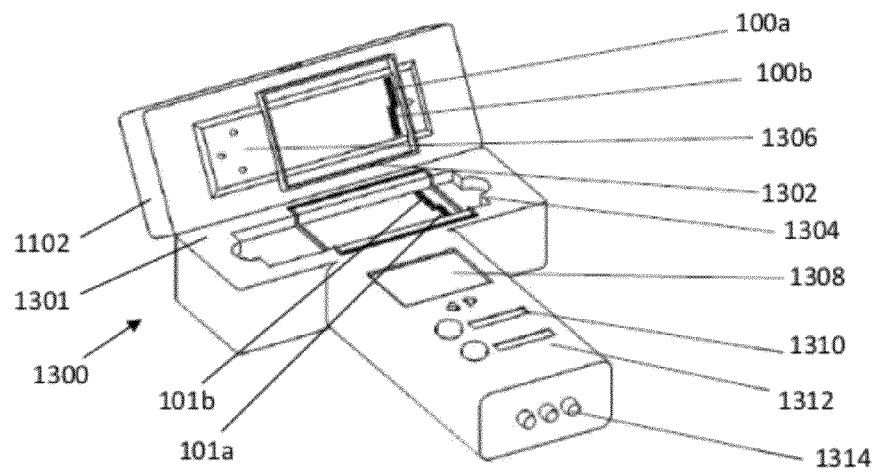
FIG. 13 is a schematic diagram of the LOC-C$^4$D portable electrophoretic system.

In the exemplary embodiment of FIG. 13, the invention provides a portable electrophoretic system 1300 that is configured to sandwich a chip (not shown) that is located in an opening 1304 (herein chip slot 1304) on a platform 1301. The chip slot 1304 is configured to allow the chip to be moved along the slot 1304 to allow a repositioning of the detection area of the chip.

The portable system 1300 includes a metal housing 1302 for shielding the detection cell of the chip. The metal housing 1302 is provided in two halves: one half extending from the cover 1102 and enclosing the top electrodes 100a, 100b, and the other half located in the base of the chip slot 1304. Once the cover 1102 is closed, the two halves make up a complete housing. Much like the embodiment of FIG. 11A, a retractable electrode mechanism is provided in the cover 1102 to retract the top electrodes 100a, 100b so that they make perfect contact with the chip when the cover clamps and secures the chip on a base of the slot 1304. The portable system 1300 also includes bottom electrodes 101a, 101b on or adjacent the base of the chip slot 1304. The arrangement of the detection electrodes on the cover and the base are such that when a chip is placed in the chip slot 1304 and the cover 1102 is in its closed position, the detection electrodes are in an operative arrangement described earlier with reference to FIG. 3.

Next to the housing 1302 are encased detector electronics which are shielded from the detection cell and from external noise to provide minimal noise and/or signal loss and easy transport. The portable device 1300 also includes a switching mechanism for alternating electrodes in operation or toggling the voltage in the reservoirs between sample injection and ion separation using high-voltage DC electrodes 1306 for electrophoresis. Also provided in the portable system 1300 are: a display 1308, an optional ground electrode acting as an electric ground to shield the detection electrodes from direct coupling, and an electronic signal processing unit comprising a signal generator and amplifier (including a potentiometer 1310 for baseline suppression and a resonator 1312 for AC generation), and a miniaturized high voltage power supply system. Specifically, for the receiving side, a battery-powered current-to-voltage converter is provided adjacent and connected to the receiving electrodes, and a rectifier, low-pass filter, and offset circuit are connected to the current-to-voltage converter. For the emitting side, a battery-powered alternating current function generator is provided adjacent and connected to the emitting electrodes, together with a miniaturized high voltage power supply. Connections 1314 are provided to interface the portable device 1300 with a computing device. By providing portability, detection or analysis can be carried out at the point of use, which obviates the need to transport samples back to a laboratory.

In one embodiment, the portable device 1300 further comprises wireless capabilities. Specifically, the device 1300 may be configured to send signals wirelessly to a personal digital assistant (PDA), a smart phone, a portable meter or the like. This may be implemented using electronics having a Bluetooth or WiFi module configured to send and/or receive signals wirelessly. The device 1300 may also operate wirelessly such that sample injections and switching on and off of the device may be controlled wirelessly.

Figure 14:
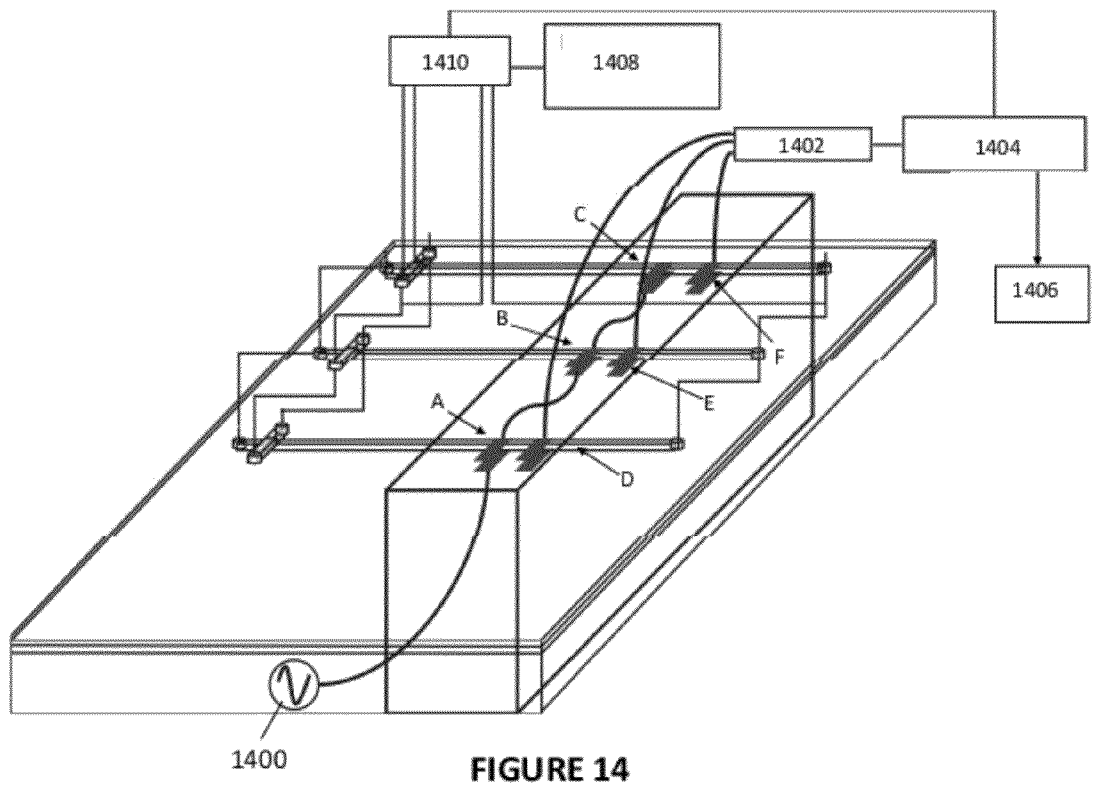
FIG. 14 is a schematic of a multiple detection cell arrangement for parallel multiple analysis.

In other embodiments, such as that shown in FIG. 14, the portable device is provided with multiple detection capabilities using multiple pairs of top-bottom electrodes where all the emitting pairs A, B and C are connected together to a single input signal 1400 and all the receiving pairs D, E and F are connected to individual receiving amplifiers and processing electronics 1402, and using a single analog-to-digital converter (ADC) 1404 with multiple inputs and a DQA system 1406 with multiple electropherograms, each corresponding to one sensor and analysis. This may be carried out by providing a microchip having multiple enclosed parallel cross channels all in one chip, which is inserted into the chip slot of the portable device to be operatively coupled in parallel to the multiple emitting and receiving electrodes in the device. A miniaturized high voltage power supply system 1408 and relays 1410 are used in this embodiment to selectively activate the separation electophoresis in the multiple enclosed parallel cross channels.

Figure 15:
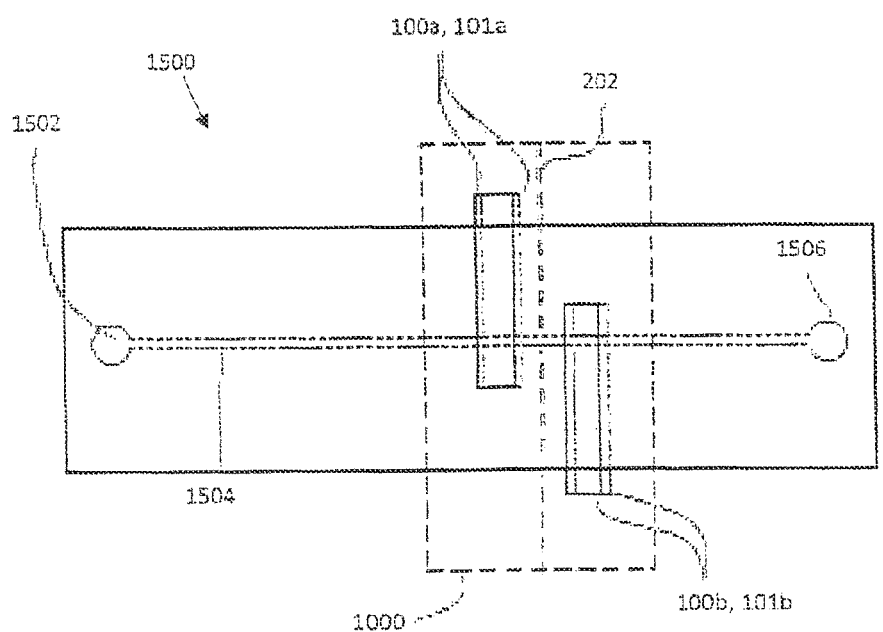
FIG. 15 is a schematic diagram showing an on-line contactless conductivity system.

Another alternative embodiment of the $C^4D$ detection cell according to the present invention is an application of the top-bottom configuration in an on-line conductivity monitoring device, e.g. for monitoring total dissolved ionized solids in water samples. This device is shown schematically as 1500 in FIG. 15. The device 1500 includes the top and bottom emitting electrodes 100a, 101a, and the top and bottom receiving electrodes 100b, 101b. A ground plane 202 is also provided together with a shielded housing 1000. Fluid for monitoring will enter the device at an inlet 1502, flow down the microfluidic channel 1504 to the outlet 1506. As will be appreciated by skilled persons, the on-line monitoring device has applications in, for example, on-line water quality control, on-line monitoring of dialysis water treatment system, on-line conductivity monitoring of haemodialysis process, chemical concentration control, etc.

Experiments

The experiments for the present invention began with the fabrication of microfluidic chips. Specifically, thin microfluidic chips were fabricated by hot embossing on polycarbonate (PC) or polymethyl methacrylate (PMMA) sheets with a thickness of only 125 μm. To emboss PC and PMMA, a hard stamp carrying the microfluidic channel features was used. The stamp and polymer were heated together on a hot plate to a temperature slightly above the $T_g$. After the stamp polymer sandwich reached the embossing temperature, a uniform pressure of 3.2-4.8 kN was applied to the chip area for 10 minutes. With the force still applied, the system was cooled below the $T_g$. On reaching this temperature, the force was released and the embossed substrate was de-molded. Sealing of the embossed channels was performed by bonding a second substrate where inlet reservoirs have been drilled in. Bonding was preformed by applying a uniform pressure, exerting 1.6 kN to the chip area at 140° C. for 20 minutes.

Electrophoresis is performed on the plastic chips. Initially the channels were preconditioned and then filled through one of the reservoirs with separation buffer: 10 to 30 mM MES-His (2-N-morpholinoethanesulfonic acid/histidine), 2 mM 18-Crown-6, and pH 6.4. Reservoirs 107, 109 and 111 (see FIG. 10) were filled with the electrophoretic run buffer solution, while reservoir 113 was filled with the sample mixture (target ions dissolved in the separation buffer).

After an initial loading, the sample was injected into the separation channel by applying potentials of +1000 V (cations) or −1000 V (anions) for 1 s to 5 s between reservoirs 109 and 113. This voltage drove the ions electrokinetically through the channels intersection, which were subsequently separated by applying a separation voltage of 2,000 to 10,000V between the reservoirs 107 and 111.

The $C^4D$ detector was formed using a pair of emitting and receiving electrodes of 1-2 mm in width displaced by 0.3-2 mm in distance. Typical AC actuation signals for the thin plastic chips and top-bottom electrode design are 10-100$V_{pp}$ at 100 to 300 kHz.

Figure 16:
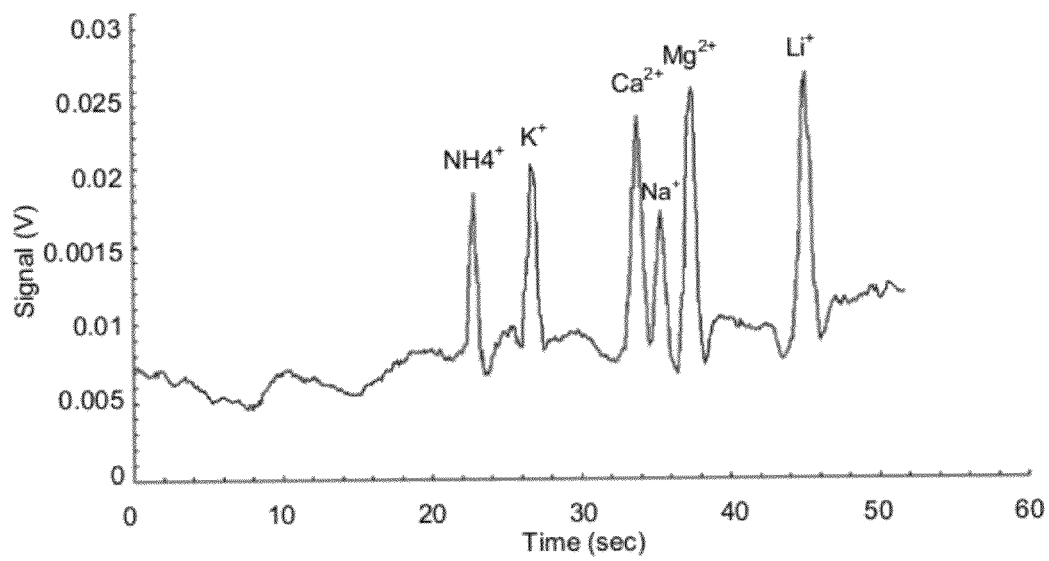
FIG. 16 is a graph showing electrophoretic analysis and conductometric detection of inorganic cations in a standard mixture containing 0.1 mM of each ion with electrode distance at 0.3 mm.

Experiments were then carried out to detect sample inorganic cations and anions. For the experiment to detect cations, the concentration of each ion was 0.1 mM (6 mg/L). as shown in FIG. 16. The experiment conditions were: injection voltage, 3000V; injection time 2 s; separation voltage 4000V; running buffer 30 mM MES-His pH 6; sinus input waveform with a frequency of 300 kHz and 50$V_{pp}$; electrode distance 0.5 mm; and electrode width 1 mm. For the experiment to detect anions, the concentration of each ion was 1 mM. The experiment conditions were: microfluidic chip 130/128 mm total/effective length; electrolyte solution 30 mM MES/His, 2 mM 18-crown-6, pH 6; injection voltage, 1 kV for 1 s; separation voltage, 7 kV; $C^4D$ detector: sine waveform of 300 kHz and 15 $V_{pp}$; electrode distance, 1 mm; electrode width, 1 mm.

Figure 17:
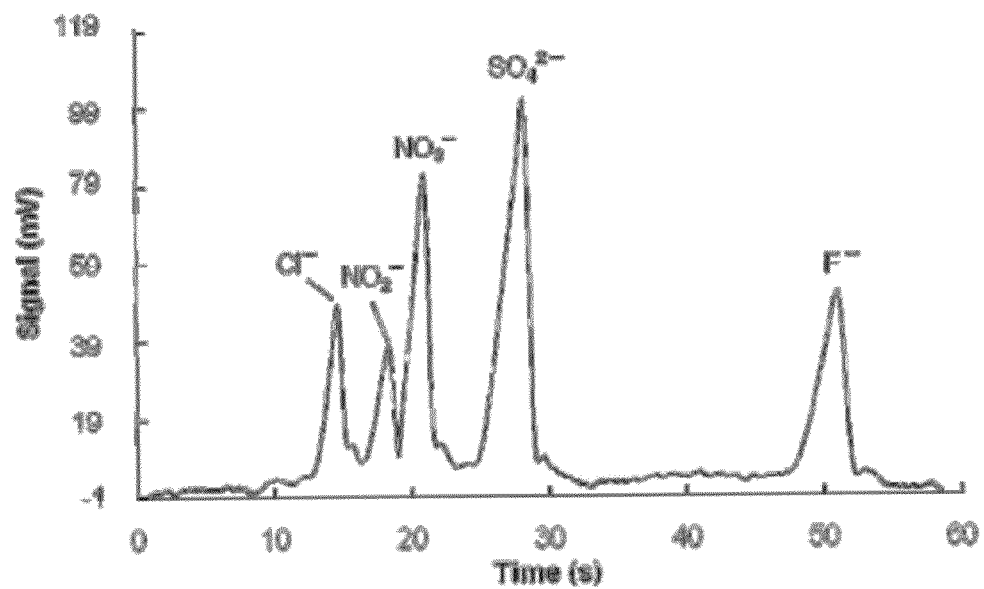
FIG. 17 is a graph showing electrophoretic analysis and conductometric detection of inorganic anions in a standard mixture containing 1 mM of each ion with electrode distance at 1 mm.

The resulting electropherogram of cations at concentration of 0.1 mM (6 mg/L) is shown in FIG. 16 (x-axis in seconds and y-axis in volts). All analyte peaks of interest were baseline resolved. The electropherogram of anions at concentration of 1 mM is shown in FIG. 17 (x-axis in seconds and y-axis in milivolts). Both figures show accurate determinations of the target ions.

Figure 18:
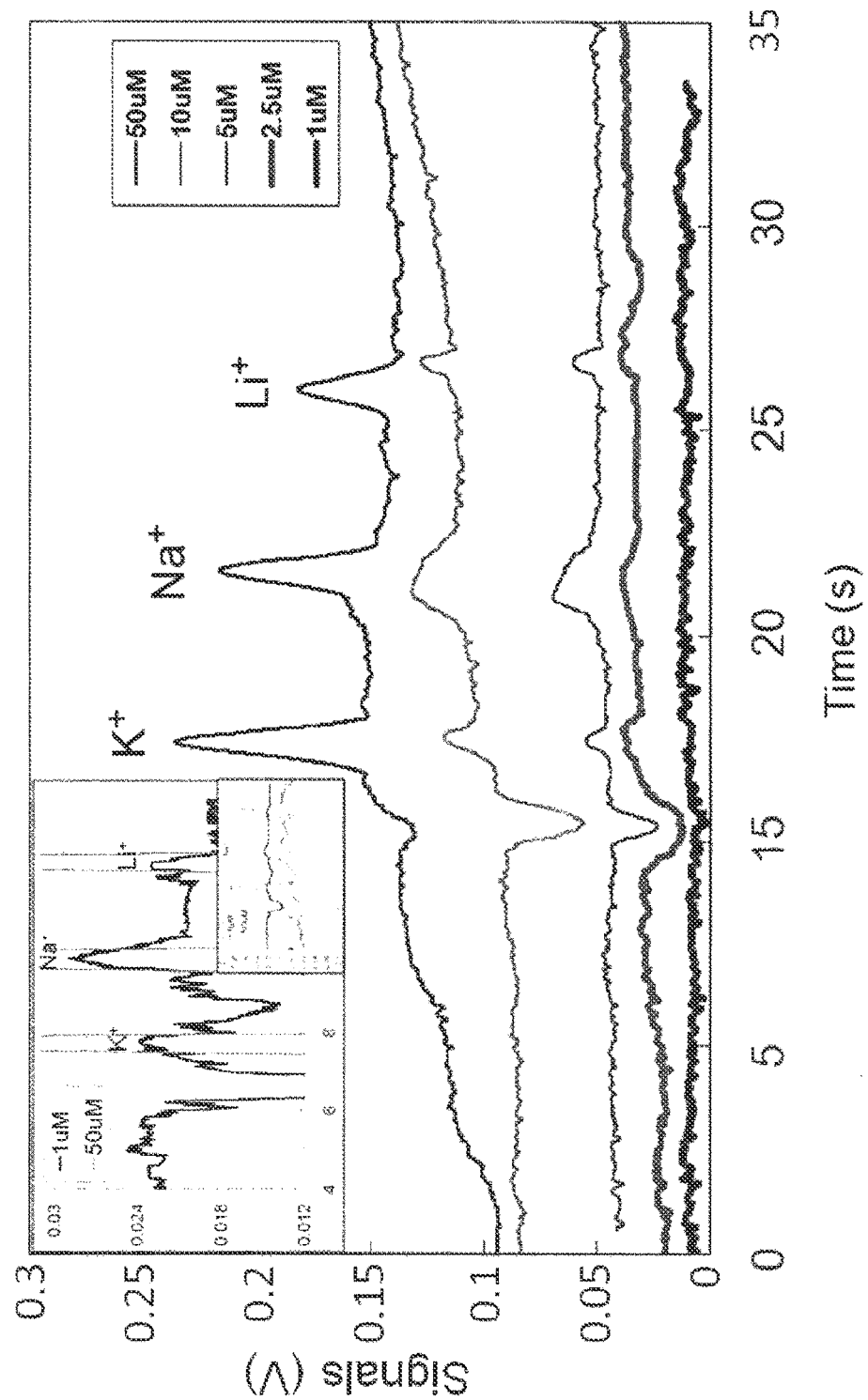
FIG. 18 is a graph showing electrophoretic analysis and conductometric detection of inorganic cations in a standard mixture containing 1-50 μm of each ion.

Referring to FIG. 18, the electrophoretic analysis and conductometric detection were carried out for inorganic cations in a standard mixture containing 1-50 μM of each ion. The experiment operating conditions were: injection voltage 4000 V; injection time 1-3 s; separation voltage 10 kV; running buffer 10 mM MES-His pH 6; sinus input waveform with a frequency of 300 kHz and 20$V_{pp}$; electrode distance 0.5 mm; electrode width 1 mm. The graph depicted shows the detected spectra for the following concentrations: 50 μM—line 1800, 10 μM—line 1802, 5 μM—line 1804, 2.5 μM—line 1806 and 1 μM—line 1808 (x-axis in seconds and y-axis in volts). FIG. 18 also shows the detection of cations at the limit of detection (LOD) of the experimental set up, i.e. LOD of 0.001 mM, 1 μM. The inset of FIG. 18 shows a magnified spectrum of the 1 μM sample (line 1808) compared to that of the 50 μM sample (line 1800).

Advantages arising from the present invention will be apparent from the foregoing description. For example, it will be appreciated that the top-bottom cell geometry allows electric field lines from each emitting electrode to be confined or focused in the detection cell volume, and signals from the detection cell volume to be optimally extracted by the receiving electrodes. This provides the present invention with improved sensitivity (i.e. the ability to detect smaller amounts of samples) over existing microfluidic based electrophoretic $C^4D$ systems. It is important to be able to provide good sensitivity at the same time as portability and be able to extend the analytical method to a bigger range of analytes including those minor elements like heavy metals.

Sensitivity is also improved by embodiments of the invention that use thin microfluidic chips, as they allow the detection electrodes to be in very close proximity to the channel to improve capacitive coupling between the AC voltage and the solution in the detection cell. This can be contrasted with known systems that use thick microfluidic chips (i.e. >1 mm thickness). When the microchips are made of thick polymer sheets, the electrodes are placed at larger distance from the channel, which causes the capacitance to drop. To address this, conventional systems provide a higher frequency input AC signal to achieve sufficient coupling between the electrodes. In general, this leads to higher stray capacitance and overall loss in sensitivity. Another conventional alternative is to increase the magnitude of the AC signal from typical values of 20-50V to $300V_{pp}$. Such a voltage, however, is difficult to handle from the point of view of safety and is impractical in portable systems.

The portable $C^4D$-LOC analytical system with optimized sensitivity requires lower inputs of voltage than previously employed to achieve low detection limits. That is to say, by increasing the electrodes' capacitance by placing the detection electrodes in a top-bottom configuration and in close proximity to the detection cell volume, and optionally improving the signal-to-noise ratio by using a ground plane in a shielded housing to eliminate crosstalk and external electrical noise, the present invention is feasibly operable on a lower power. This is a particularly important advantage for portable systems since a high AC voltage is dangerous to handle and the instrumentation required to produce such high signals can be prohibitively bulky.

Where a shielded housing is implemented, further improvements in sensitivity and thus LOD can be obtained since the $C^4D$ detection cell is further isolated from the high voltage, environmental noise and artifacts. This can be contrasted with known $C^4D$ detectors that do not implement a shielded housing and that accordingly suffer from much higher LODs.

Where the electrode arrangement of the invention is implemented using external electrodes (i.e. not integrated with the chip) with adjustable distance integrated into a shielded housing, a robust and low-cost process is provided for the fabrication of the detection cell. This avoids the cost and complexity of micro-fabrication processes.

The foregoing describes a first set of preferred embodiments, which, as will be understood by those skilled in the art, may be subject to variations or modifications in design, construction or operation without departing from the scope of the claims. For example, while most embodiments have been described with reference to electrophoresis, this is not essential. As described with reference to FIG. 15, the detection cell or detection system may be used for non-electrophoresis purposes (e.g. liquid chromatography, stand alone conductivity sensor). Also, in terms of electrode arrangement, while the figures show electrodes aligned to the channel, this is not essential. All that is required is for the electrodes to cover and be adjacent the channel so that signal coupling is achieved as described earlier. The position of the electrodes with respect the channel is not critical and signal coupling can be accomplished when the electrodes cover totally or partially the channel width. It will also be appreciated that while the term top-bottom has been used to describe the electrode geometry, the invention is not limited to the top and bottom areas of the channel; an opposing-sides placement as shown in FIG. 8 is also encompassed. Also, the electrodes need not be positioned flat on the microfluidic chip but may, where necessary or desired, be positioned vertically (i.e. so the edges of the electrodes are adjacent the channel). The above variations, for instance, are intended to be covered by the scope of the claims.

Additional Preferred Embodiment

Figure 19:
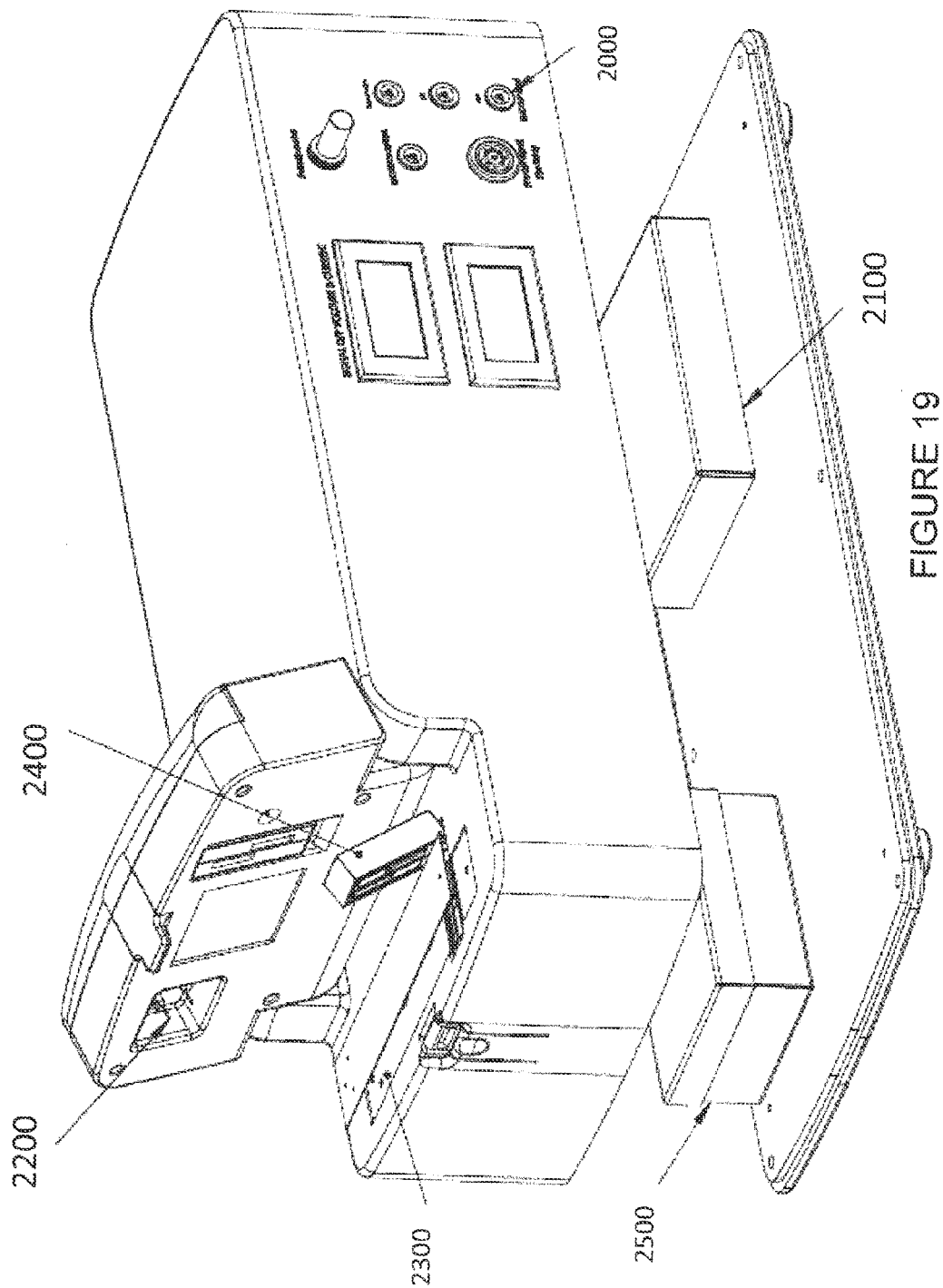
FIG. 19 is a schematic view of a portable LOC analyser which is a further embodiment of the invention.

Another aspect of the present invention is a compact portable lab-on-a-chip analytical instrument based on electrophoresis integrated with a $dC^4D$ detector. The portable instrument is shown schematically in FIG. 19. The instrument comprises two sections: main body housing and a fluidic compartment. The housing accommodates the instrument electronics including the signal input/output devices 2000 (the output devices generate a signal to send to a computer or PDA) and signal processing electronics 2100. The front top part of the instrument housing has a lid, and opens up to a fluidic compartment where the fluid chip is placed in the chip stage 2300 and high voltage (HV) is applied by means of HV electrodes 2200 (to supply voltage to a microfluidic chip on the chip stage 2300 when the lid closes), and electrophoresis and $C^4D$ detection is performed on the chip by a removable detection cell cartridge 2400.

Main Body Instrument Electronics

The instrument is lodged on a housing containing the analytical hardware and processing electronics in the instrument. The hardware and electronic circuit boards include the input signal generator and amplifier 2500, signal processing electronic circuit 2100, relays switching, and miniaturized HV power supplies. The details of the components are shown schematically in FIG. 20. This main body housing is shielded to prevent from interference and for noise reduction. The device and components are designed to be powered by ±15 Volts or ±5 Volts batteries. Two sealed lead acid rechargeable batteries less than 0.5 kg in weigh and life time more than 20 hrs are used one to feed the electronics and the other for the HVs electrophoresis power supplies. The electronics section consists of pickup amplifier that collects the signals from the pickup electrode and converts them to voltage while amplified and then transfer them to rest of the electronics for further processing. This analytical signal from the cell is a very weak current in the order of nA. Compared to commercial systems available, we carried out novel engineering to pickup and collect this current very carefully. A combination of improved self latching connectors plus shielded gold plated electrodes connected to self-latching pins with minimal capacitive effects but perfect and tight contacts provide the perfect low noise signal pickup, low loss, and safe signal transfer into the rest of the system. The current is transferred to the pickup OPA through coaxial cables to reduce any Interference from outside. The pickup OPA electronics are placed in very close proximity to the pick up electrode for minimal signal loss. The contacts are made to the shielded $dC^4D$ cell by means of short coaxial cables and low capacitive surface mount self latching plugs and jacks. The self latching mating and unmating feature provides perfect electrical contact against vibration, shock, pull, and facilitates miniaturization and operation is small areas.

The stability of the output signal is dependent on the stability of the supply voltage of the electronic components (±Vin). One approach is to put capacitors from the positive and the negative power supply rail to ground to keep the supply voltage stable when the IC chips change their current consumption (the supply paths on the PCBs have a small resistance so to get a low voltage drop when current flows). Otherwise one might see oscillations and other artifacts One typically puts 10 µF (tantalum) on each printed circuit board and 100 nanoF (foil) for each IC, right next to the supply pins. Here a new generation of tantalum capacitors NeoCapacitor® (NECTOKIN) that employ a conductive polymer, has excellent noise-absorbing characteristics were added to all the circuits next to the ±supply voltage of every IC components. Every section of the device in general is sealed within the grounded housing and the only signal transfer is through low loss coaxial cables connected to surface mount miniaturized plugs and jacks. The output signal of the pickup amplifier is transferred to signal processing circuit for further rectification, low pass filtering and suppression to zero level. All the electronics are low noise and miniaturized surface mount components with 4 layers of grounding and double sided boards for eliminating signal interference between circuits or capacitive effects which are source of noises of these type of circuits with frequencies as high as 100-300 kHz typically used for $C^4D$ sensors. The input signals are 10 to 20 $V_{pp}$ and can be amplified to 250 $V_{pp}$ using HV amplifier.

The double sided PCB electronic circuit is constructed to have high frequency sensitive components on both sides of the PCB which has dual grounding in between. This provides a high degree of shielding and isolation within different components at the same time that reduces the space needed to house the circuits. The connections are made through the board which allows a very short distance connection improving shielding. This is especially important for the pickup amplifier electronic circuit where the feedback resistor converts the pickup current to voltage and is completely shielded from the OPA itself therefore, ensuring minimal signal interference.

Figure 20:
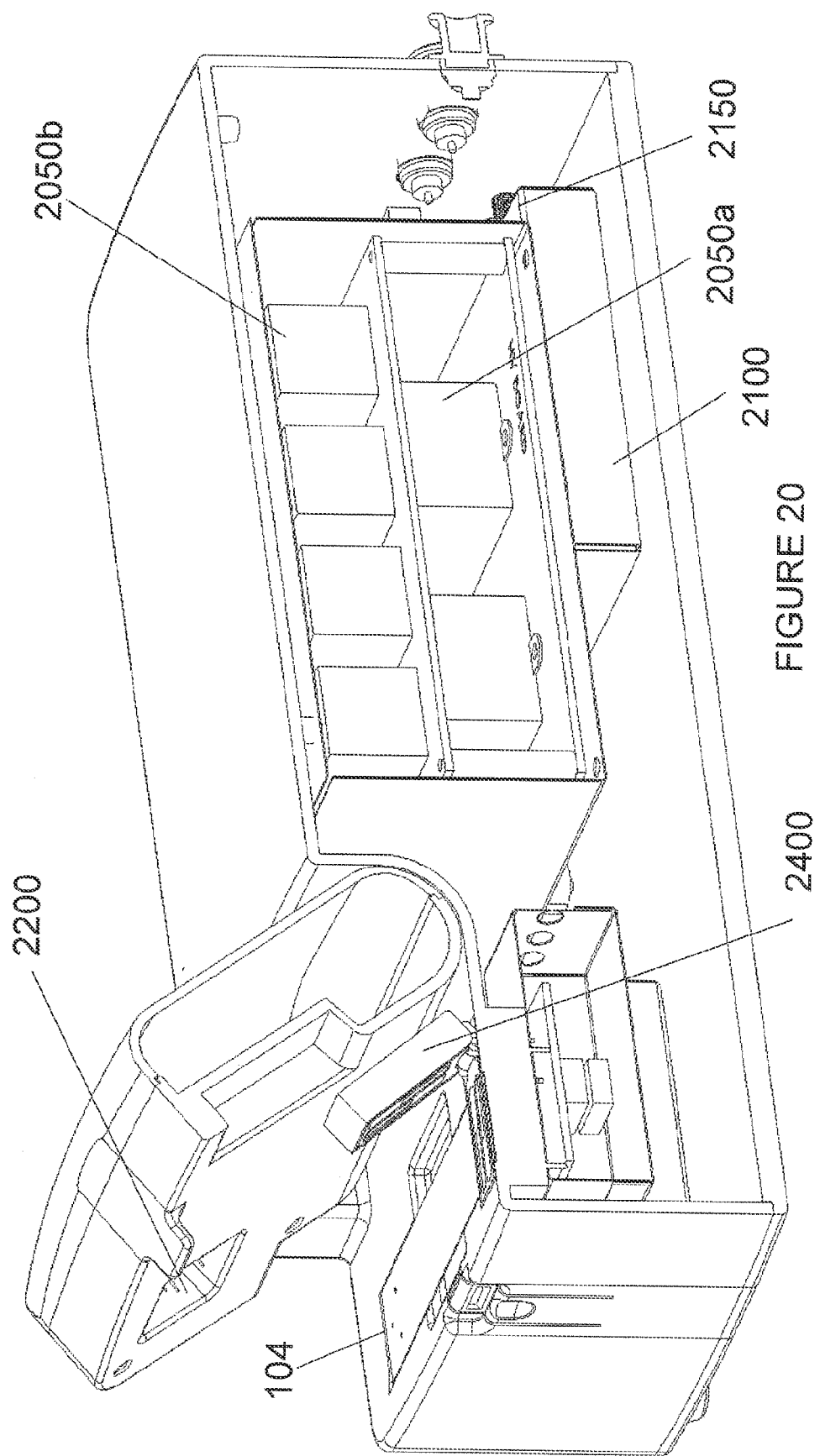
FIG. 20 is a detailed sectional view of the E-dC$^4$D device with hardware and electrophoresis components.

FIG. 20 is a sectional view of the E-$dC^4D$ device with hardware and electrophoresis components. The $C^4D$ hardware includes: a dual $C^4D$ cell cartridge 2400, pickup signal electronics 2450, signal generator 2500, signal processing electronic circuit 2100, and USB connector 2150 to a computer DAQ card for signal transfer and auto control of the system using a laptop. The electrophoresis hardware includes a plastic chip 104, high voltage power supplies 2050a, high voltage relays electronics 2050b, and electrophoresis high voltage electrodes 2200.

Fluidic Electrophoretic Compartment

Figure 1:
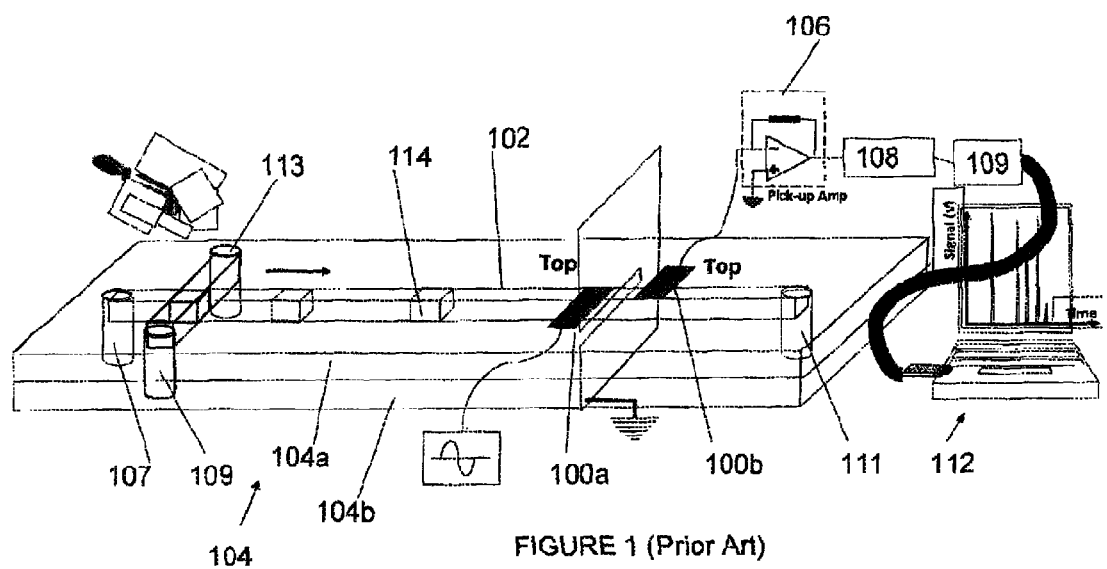
FIG. 1 is a schematic diagram of a conventional LOC-$C^4D$ analytical system comprising an electrophoretic separation microchip and $C^4D$ detection electrodes.
Figure 2:
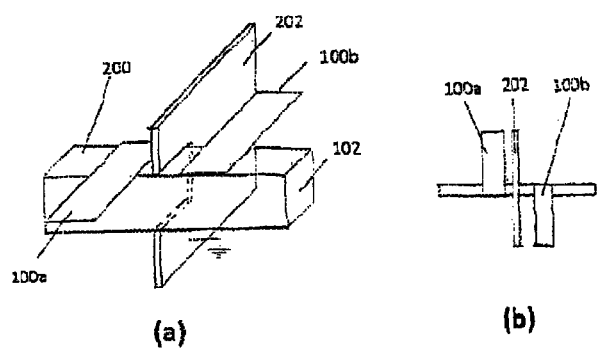
FIGS. 2(a) and 2(b) are diagrams of a conventional $C^4D$ detection cell electrode arrangement.
Figure 21:
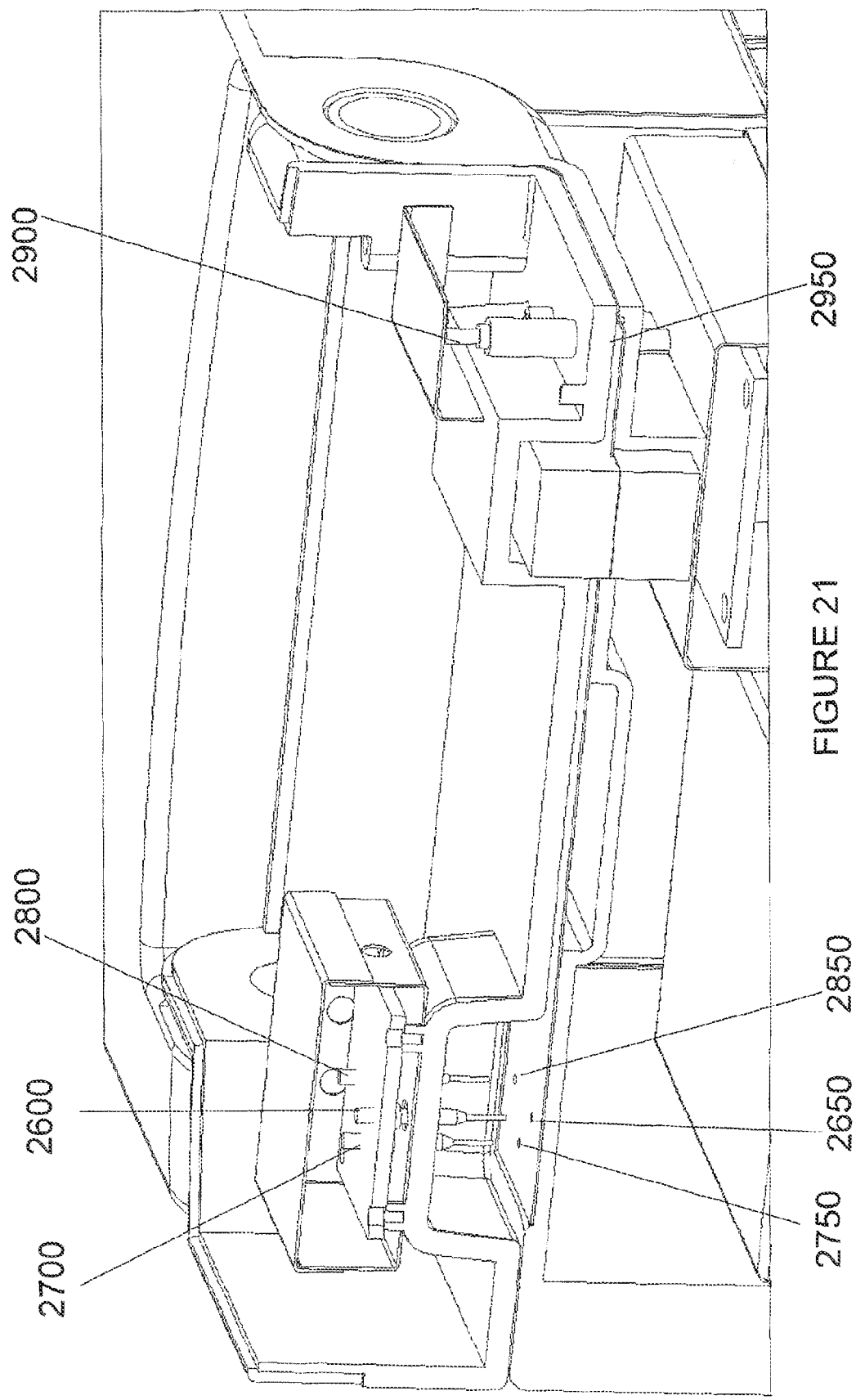
FIG. 21 is a schematic of the analyzer showing the high voltage electrodes pins aligned on the chip with shielded housing.

The analytical fluidic operations are accessed by opening a top lid 2200 on the instrument. In this compartment, the microfluidic chip 104 is placed on the chip stage 2300. High voltage to perform electrophoresis is applied from four miniaturized power supplies by the means of four pins 2600, 2700, 2800, and 2900 positioned on the top lid to coincide with the microchip liquid reservoirs, as shown in FIG. 21. The corresponding reservoirs are sample (2650), buffer (2750), sample waste (2850), and buffer waste (label 2950 indicates the general position of this reservoir, but the buffer waste is not visible in the figure as the cover is closed; note, however, that the corresponding component 111 of the first embodiment is clearly visible in FIG. 1).

The application of High voltage (HV) is computer controlled and allows performing the operations of sample injection and separation. During these operations the lid is kept closed for the HV pins to establish electrical connection with the solution which at the same time isolates and prevents the user from contact with the High voltage (HV) avoid and any electric shock hazard. Ultra miniaturized high voltage power supplies with dual polarity of ±0.5 kV up to 5 kV are used. The potentials at all four electrodes can be controlled independently. The output of the power supplies is proportional to the input voltage range from 0.7V up to 5V and can be controlled directly via computer DAQ card. The Injection and separations are computer controlled using a code written in LabVIEW. The software allows controlling separation and injection voltage level and time. It also allows to create different sample injection protocols, such as, cross-injection, L-injection (two power supplies), or pinch-injection (using four power supplies).

As safeguard mechanism an external feedback circuit loop is employed to prevent excessive current passing through the DAQ card. To provide a perfect electrical ground for the injection and separation voltage during electrophoresis, one of the four power supplies connected to the ground reservoir is set to slightly less than 0V, i.e. negative voltage to sink the currents from the other HV supplies toward the ground reservoir and prevent any reverse flow toward other reservoirs.

The microchips used in this system are of 250 μm in thickness or less for effective signal coupling and detection. The thin microchips improve the capacitive coupling between the AC voltage and the solution found in the cell. This lowers the requirements for high voltage or high frequency. The detection is performed on the second half of the chip by a dual-$C^4D$ detection cell.

$C^4D$ Detection Cell Cartridge

Figure 22:
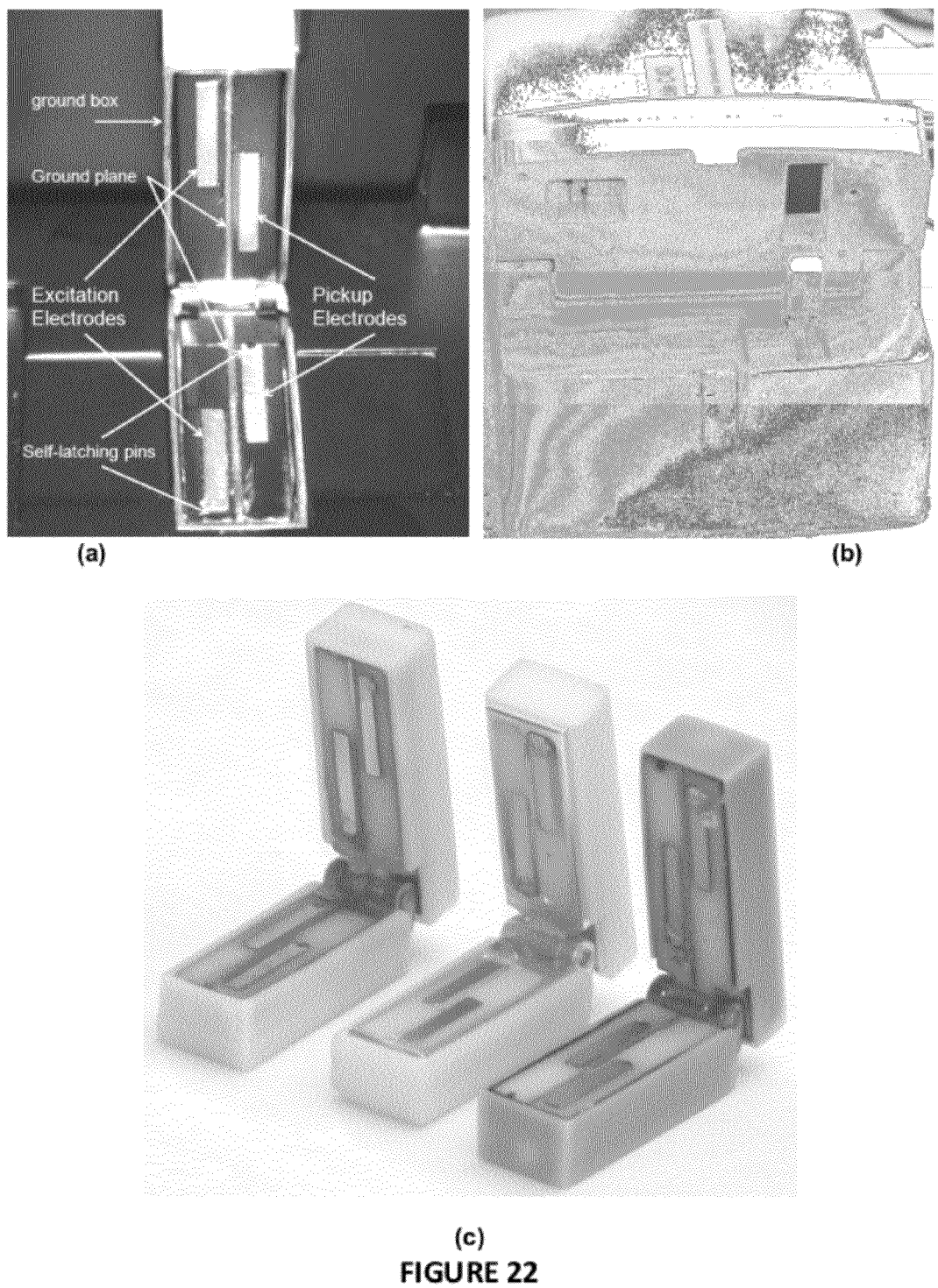

FIG. 22 (a)-(c) show replaceable $dC^4D$ cartridges with top-bottom excitation and pickup electrodes with a ground plane in between. These components are positioned precisely within a small Faraday cage with an external surface isolated by a polymer. A Faraday cage or shield is an enclosure formed by a conducting material or by a conductive mesh. The enclosure blocks out external non-static electric fields.

Figure 23:
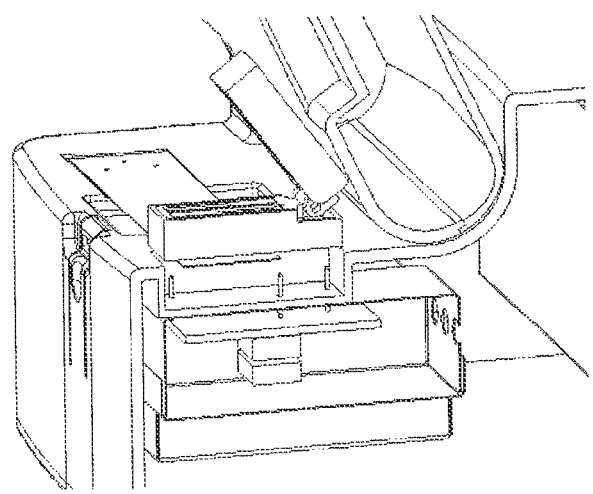
FIG. 23 illustrates how the cartridge cell is aligned for subsequent connection to the analyzer housing by a downward motion, using three pins of the housing to transmit the input signal, pickup signal, and a ground signal.

The cell design is based on the embodiments described earlier, which are also described in co-pending U.S. Ser. No. 13/057,922, which is the dual top-bottom cell configuration. The cell box is attached close pack to integrated pickup electronic circuits. The cartridge can be plugged in and out using self-latching contact system, which makes perfect Ohmic contact with the cartridge cells as illustrated in FIGS. 23 and 24 described below.

The $dC^4D$ detection cell is based on the concept of replaceable exchangeable cartridge. This is a unique feature in the $dC^4D$ detection cell that allows selecting the appropriate cell electrode dimension to the analytical problem to adjust resolution and sensitivity. The $C^4D$ cell of the present invention is connected to a battery-powered alternating current function generator, which allows for portability of the lab on a chip analyzer. FIG. 22 (a)-(c) shows images of the cartridge cells. Sensitivity and resolution depend highly on the cell design and importantly on electrode dimensions and gap distance. These dimensions affect these two parameters in an opposite manner. Hence, the different cartridges are designed with specific dimension to provide with higher sensitivity or high resolution depending on the application requirements.

Figure 24A:
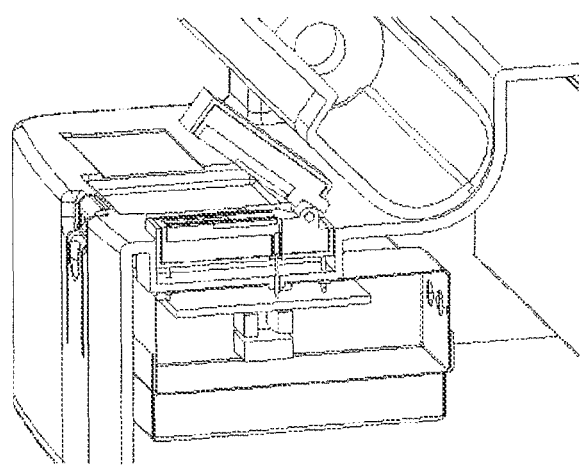
FIGS. 24 (a) and (b) illustrate the self-latching contacts that fix the cell with perfect contact tightly free from vibration, loose contact or misalignment.
Figure 24B:
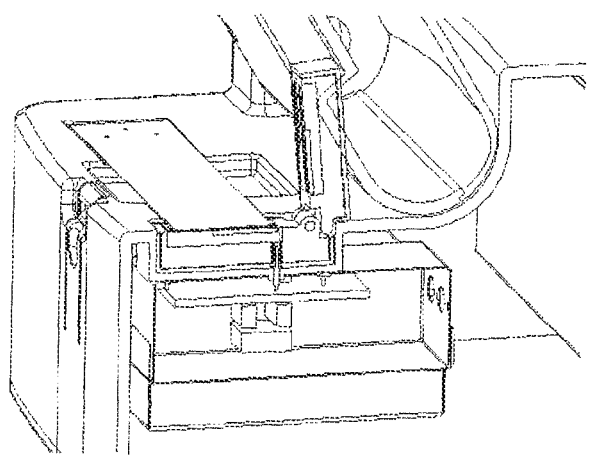
Figure 25:
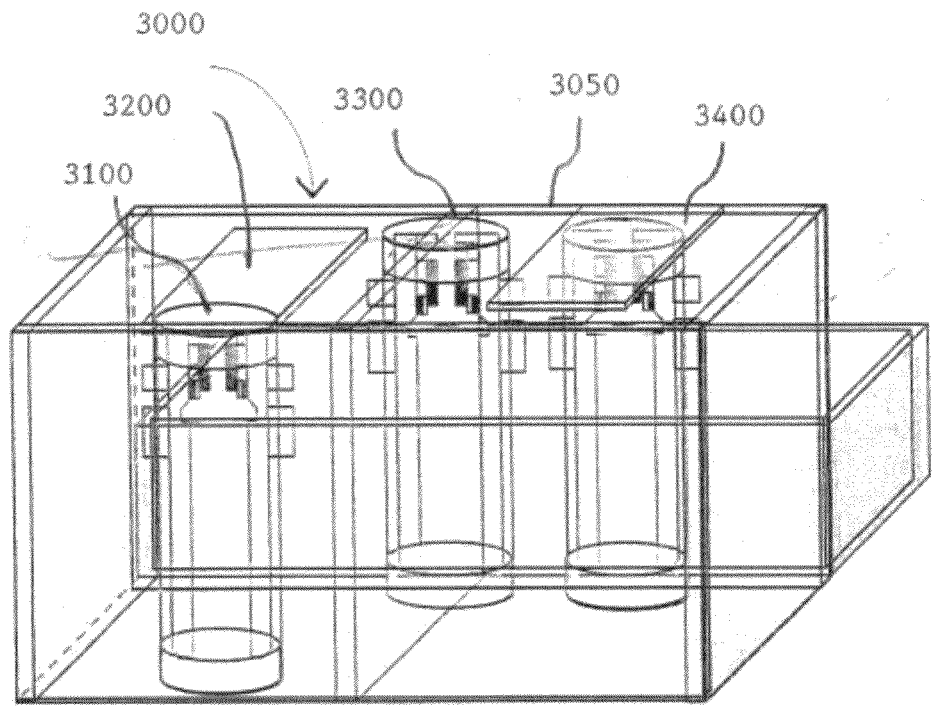
FIG. 25 (a) is a schematic diagram of the one side of the dC$^4$D cartridge showing the details of the electrodes and ground plane connections.
Figure 25:
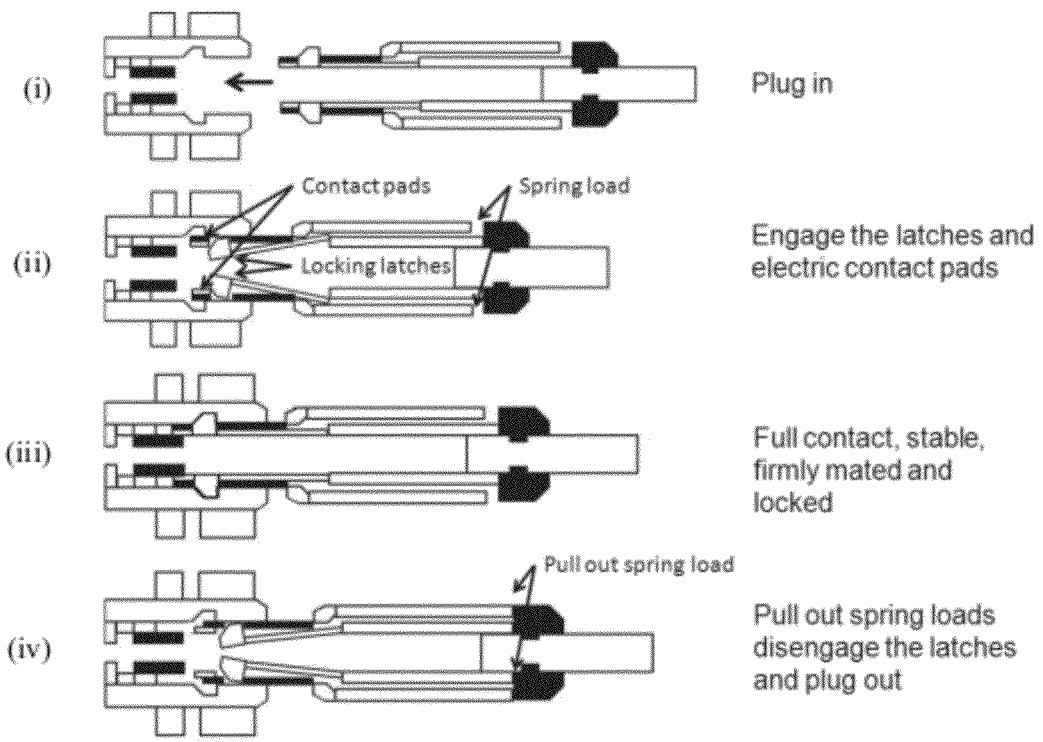

The cartridge encloses the detection cell and consists of a pair of top-bottom excitation electrodes and a pair of top-bottom pickup electrodes encased in a rectangular metal box (of typical dimensions: 1×1.5×3.5 $cm^3$). The excitation and pickup top-bottom electrodes are well aligned and the bottom ones are connected through pins underneath in the housing to their respective sources by a self-latching mechanism, as shown in FIG. 24, and in more detail in FIG. 25(b). Initially the cartridge cell is put into the position shown in FIG. 23. Then, it is moved downward to plug it in: first to the position shown in FIG. 24(a), and then the position shown in FIG. 24(b) in which it is locked in position by the self-latching mechanism. The cartridge cell with three pins that is to contact to input signal, pickup signal, and ground is plugged in from top. The schematic of $dC^4D$ cell construction is shown in FIGS. 25 (a) and (b). The top lead contains the set of top excitation electrode, pickup electrode and groundings all are aligned to face exactly to bottom pair and contact the fluidic chip upon closing. To eliminate any loose contacts or capacitive gaps which are source of noises, a spring load in the box lead is constructed to push the top lead against the bottom providing very close contact to the fluidic chip. The detection cell is fabricated by electroplating to achieve precise geometrical dimensions of the electrodes and shield plane. The parts are then embedded on a polymer matrix for isolation. The precise microfabrication of the electrodes and ground plane eliminates the electric field non-uniformity, noise, and direct coupling or stray capacitance which is highly important for improving sensitivity and enhancing the detection limit of the system. The ground plane isolates the entire space between the electrodes like a wall such that it separates the cell metal box into two absolutely isolated sections for the emission electrodes and pickup electrodes (FIG. 24). These are connected to the electronic circuit through gold plated pins. The pins allow the cartridge to be plugged in and out with minimal signal distortion or any loss. The precise and closed pack cell with a ground plane separating the electrodes or excitation and pick up sections of the cell, eliminates the stray capacitance between the electrodes.

The cartridge is designed to sandwich the chip placed in the chip holder and to press the electrodes against the surface of the chip to provide maximum proximity and avoid air gaps. The cell allows for maximum signal coupling with minimal noise of less than 0.5 mV. To protect the pickup signal and to eliminate signal loss the pickup amplifier were housed just underneath the detection cell connected to the pin in contact with pickup electrodes. The double sided high density circuit boards are used to place some sensitive components on opposite sides of the printed circuit boards with grounding. The signal transfer was performed by shielded coaxial cable that was solder-contact to eliminate any external capacitive noise. The dC$^4$D detection cell is isolated from electronic noises and induces the confinement of field lines with in the detection cell. The ground plane eliminates direct coupling (i.e, stray capacitances) that completely divide the cell into two compartments the excitation and pickup compartments. Therefore, the distance for the signal to be transported between different components is minimal and signal losses are reduced.

FIG. 25 (a) is a diagram of the one side of the dC$^4$D cartridge showing the details of the electrodes and ground plane connections. In FIG. 25 (a), the cartridge cell 3000 has three sockets to receive pins which electrically transmit an input signal, a ground plane between the electrodes, and pickup signal. The cartridge cell 3000 is plugged in from the top. The cartridge cell has an outer wall 3050 which is electroplated metal and is grounded in use. The top lead contains the set of: a top excitation electrode 3200, a ground plate 3300 between the electrodes, and a pickup electrode 3400. Each of these element has a corresponding pin contact (e.g. the top excitation electrode 3200 has the pin contact 3100), which is at the top of a respective socket. All the sockets are aligned to face in use towards a corresponding pin (plug) of the housing, and contact is made in each socket upon inserting the cartridge cell 3000 into the housing. The plugs and sockets provide a self-latching mechanism, which locks the pins to the cartridge cell. In FIG. 25(a) the ground plane isolates entirely and divides the cell to two parts. One is for the excitation electrode and pin connection, and the other is for pickup signal entirely by the pick up electrode and pin connection.

FIG. 25 (b) is a diagram of the pin self-latching mechanism to contact the cell to input output signals and ground. Contacts pads of the pins are brought into contact with the fix pads of the housing pins and the locking latches fix them. A spring load pulls the locks inward and disengages the latches for pull out. The dimension of the pins in the cell is cylinders of 2 mm diameter×15 mm length. Specifically, FIG. 25 (b) shows the mechanism of one of the plugs (i) approaching the respective socket, (ii) engaging the latches and electric contact pads, (iii) locking into the respective socket, and (iv) disengaging by pulling out the spring loads.

As shown in FIG. 25(b), the self-latching contacts fix the cell with perfect contact tightly free from vibration, loose contact or misalignment. The self-latching contacts or connectors provide perfect Ohmic contacts and is tight and vibration free.

EXAMPLES

The analytical capability of the portable electrophoretic E-dC$^4$D system was investigated in three fields of application: water quality control (i.e., analysis of cations in water); food analysis: analysis of organic acids and preservatives in fruit drinks; and bio analysis (i.e., DNA PCR fragment analysis).

Analysis of Cations in Water

Figure 26:
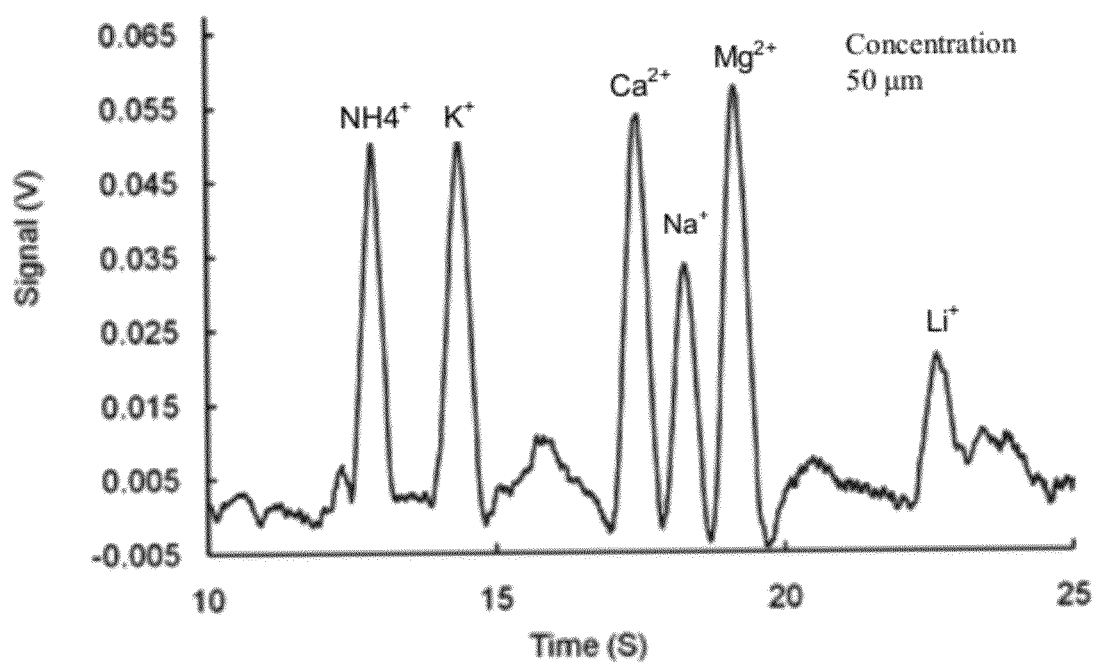
FIG. 26 is a graph of the electrophoretic analysis and conductometric detection of $NH_4^+$, $K^+$, $Ca^{2+}$, $Na^+$, $Mg^{2+}$ and $Li^+$ cations in a standard mixture containing 50 μM of each ion.

FIG. 26 displays the electropherogram of $NH_4^+$, $K^+$, $Ca^{2+}$, $Na^+$, $Mg^{2+}$ and $Li^+$ cations at concentrations of 0.1 mM using a 30 mM MES/His buffer. The full width half maximum-values for the analytes peaks at 0.1 mM are 0.8, 0.8, 0.9, 0.8, 0.9, to 0.9 s and for 0.5 mM are 1.05, 1.06, 1.27, 1.49, 1.36, 1.43 s respectively, which is in a well defined range for a high resolution analytical system. Calibration curves for these six inorganic cations were determined to be linear for concentrations range of 0.01 to 1 mM.

FIG. 26 shows the electrophoretic analysis and conductometric detection of $NH_4^+$, $K^+$, $Ca^{2+}$, $Na^+$, $Mg^{2+}$ and $Li^+$ cations in a standard mixture containing 50 μM of each ion. Operating conditions: microchip 8.5/7 cm total/effective length; electrolyte solution, 20 mM MES/His, 2 mM 18-crown-6 pH 6; injection voltage, 4 kV for 3 s; separation voltage, 4 kV. C$^4$D detector: Sine waveform of 300 kHz 20 $V_{pp}$; electrode gap, 1 mm; electrode width, 2 mm.

Figure 27:
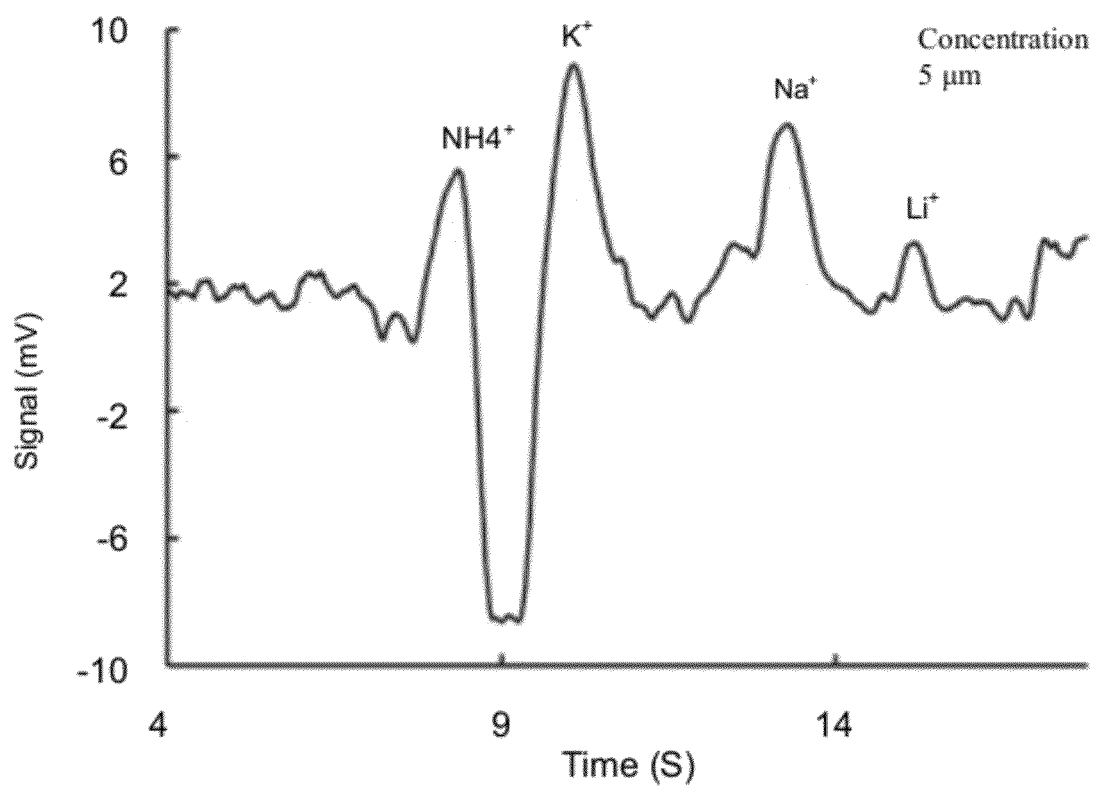
FIG. 27 is a graph of the electrophoretic analysis and conductometric detection of $NH_4^+$, $K^+$, $Na^+$, and $Li^+$ cations in a standard mixture containing 5 μM of each ion.

FIG. 27 shows the electrophoretic analysis and conductometric detection of $NH_4^+$, $K^+$, $Na^+$, and $Li^+$ cations in a standard mixture containing 5 μM of each ion. Operating conditions the same as above.

Food Analysis: Analysis of Organic Acids and Preservatives in Fruit Drinks

Figure 28A:
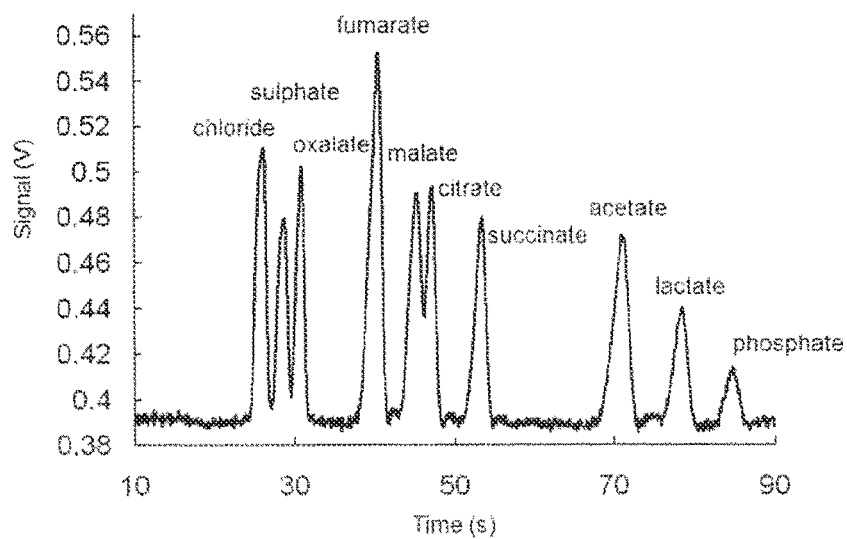
FIG. 28(a) and (b) are graphs illustrating the simultaneous detection of organic acids (10-80 mg/L) in a standard sample and in bottled fruit juice.

Ten commonly found organic and inorganic anions in beverages namely chloride, sulfate, oxalate, fumarate, malate, citrate, succinate, acetate, lactate and phosphate were examined. Experimental conditions were carefully optimized as a large number of analytes was examined. The best background electrolyte for good sensitivity and separation was achieved by 10 mM His and 7 mM glutamic acid at its natural pH. Electropherograms of the separation of the 10 common organic and inorganic anions in a standard solution and in an apple and aloe vera fruit juice are depicted in FIG. 28(a) and (b) respectively. The electrophoretic conditions were microchip 85 mm total length, background electrolyte 10 mM His, 7 mM glutamic acid (pH 5.53); separation voltage −4 kV, injection voltage −4 kV for 1 s.

FIG. 28(a) illustrates the simultaneous detection of organic acids (10-80 mg/L) in a standard solution. The peak description, and concentrations in mg/ml are: 1, Cl$^-$(0.01); 2, $SO_4^{2-}$ (0.01); 3, oxalate (0.01); 4, fumarate (0.03); 5, malate (0.03); 6, citrate (0.03); 7, succinate (0.03); 8, acetate (0.05); 9, lactate (0.05); 10, phosphate (0.08).

Figure 28B:
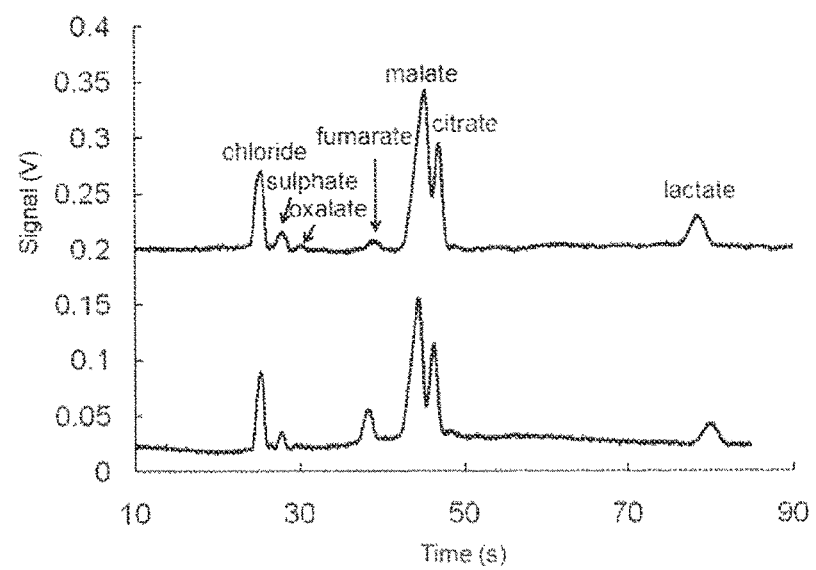

FIG. 28 (b) are electropherograms of apple and aloe vera fruit juice. The upper line is apple and aloe fruit juice at a dilution of 1:50, and the lower line is the same apple and aloe vera fruit juice spiked with fumarate to confirm the identity of the fumarate peak.

Malate, citrate and lactate anions are expected in the apple juice as major anions as stated on the beverage packaging. Chloride and sulfate were also previously identified as trace ions in fruit juice samples. The upper trace (in FIG. 28(b)) shows the separation of the anions in the diluted apple juice and chloride, sulfate, malate, citrate and lactate ions were identified together with a small peak corresponding to fumarate. Apple juices are known to contain various concentrations of fumaric acid naturally and due to processing. Peak confirmation was carried out by spiking with a 30 mg/L of fumarate solution the diluted fruit juice. From the lower trace, it can be confirmed that the unknown peak is that of fumarate.

Analytical parameters such as the RSD (%) of migration time, peak heights and peak areas as well as the $r^2$ values of the ten organic and inorganic anions are summarized in Table 1. The RSD (%) values are based on six consecutive injections of 0.01 mg/ml of $Cl^-$, $SO_4^{2-}$ and oxalate, 0.03 mg/ml of fumarate, malate, citrate and succinate, 0.05 mg/ml of acetate and lactate, and 0.08 mg/ml of phosphate.

The RSD values for migration time are all well below 3% and thus, good reproducibility is shown. The RSD values for peak height and peak area are all lower than 5%.

TABLE 1

RSD (n = 4) of migration time (RSD($t_M$) %), peak height (RSD(PH)), and peak area (RSD(PA)), correlation coefficients ($r^2$), and LOD for the microchip $C^4D$ separation of inorganic and organic anions and quantitative analysis of apple and *aloe vera* juice sample (in mg/ml)

| | RSD (tM) % | RSD (PH) % | RSD (PA) % | r2 | LOD | Apple Juice |
|---|---|---|---|---|---|---|
| Chloride | 1.37 | 0.60 | 2.28 | 0.9993 | | 5.57 ± 0.44 |
| Sulfate | 2.11 | 1.03 | 3.71 | 0.9802 | | 0.91 ± 0.10 |
| Oxalate | 2.14 | 2.38 | 1.93 | 0.9937 | | ND |
| Fumarate | 1.80 | 0.49 | 1.54 | 0.991 | | 1.39 ± 0.48 |
| Malate | 1.56 | 1.93 | 0.65 | 0.9977 | | 50.80 ± 0.66 |
| Citrate | 1.59 | 1.66 | 1.94 | 0.9959 | | 27.56 ± 0.45 |
| Succinate | 1.41 | 4.40 | 0.71 | 0.9997 | | ND |
| Acetate | 2.69 | 4.25 | 1.85 | 0.9923 | | ND |
| Lactate | 2.40 | 5.01 | 4.76 | 0.9989 | | 43.00 ± 16.69 |
| Phosphate | 2.48 | 3.81 | 5.73 | 0.9955 | | ND |

Figure 29:
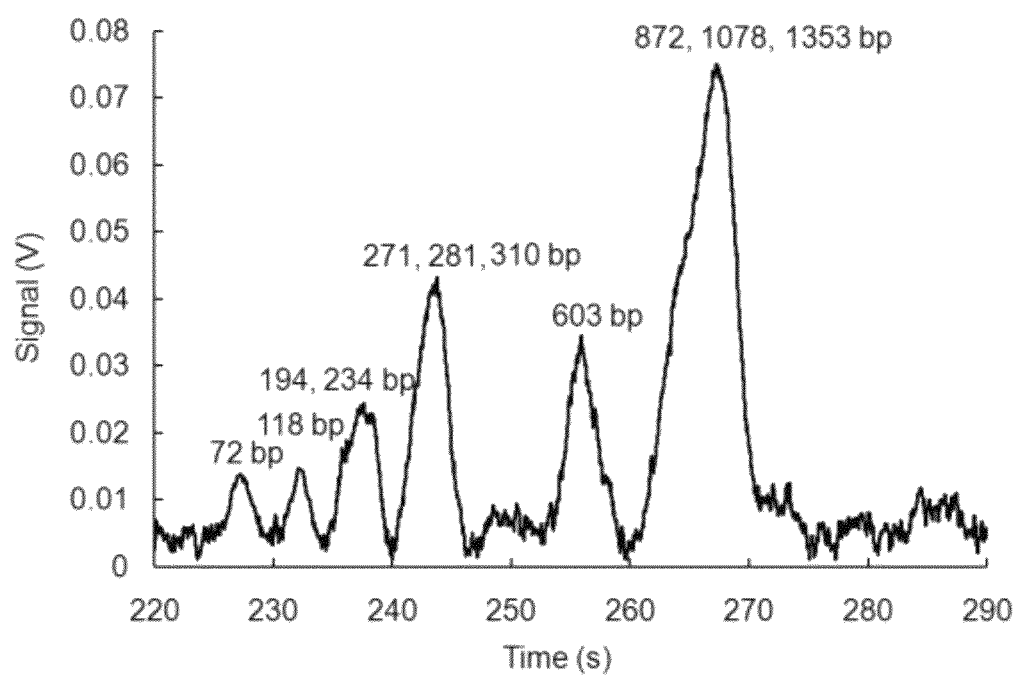
FIG. 29 is a graph of the electrophoretic analysis of 11 base pairs Hae DNAs 72, 118, 194, 234, 271, 281, 310, 603, 872, 1078, and 1353 bp, respectively, with concentration of 25.6 μg/ml in water in CHESTris buffer 2% PVP by E-dC$^4$D.

Values are in mg/L and each value is a mean value of six measurements, RSD (n=6), ND, not detected. Determined using peak area for electrokinetic injection at −4 kV for 1 s.
Bio Analysis: DNA PCR Fragment Analysis The size analysis of DNA fragments has been also carried out in the system and it is shown in FIG. 29. The $dC^4D$ detector captured the signal corresponding to the fragments; hence the detection of DNA was performed directly without the need for markers or labeling.

FIG. 29 is a graph of the electrophoresis of 11 base pairs Hae DNAs 72, 118, 194, 234, 271, 281, 310, 603, 872, 1078, and 1353 bp respectively with concentration of 25.6 ug/ml in water in CHESTris buffer 2% PVP by E-$dC^4D$. The experimental conditions were an excitation frequency at 300 KHz and amplitude of 74.1 Vpp. Injection between sample reservoir and last reservoir as ground was carried out using −3.5 kV for 1 second and the separation between buffer reservoir and last reservoir as Ground with −3.5 kV.

The $C^4D$ detection cell of the present invention allows for low background noise and low limit of detection (LOD). The portable lab-on-a-chip analytical instrument based on electrophoresis as a separation technique allows for simultaneous detection of ionic compounds, including trace elements. The present invention due to its improved capacitive coupling requires a much lower signal amplitude for the input excitation AC signal than previous version. This is an advantage due to safety concerns because an AC voltage of 300 Vpp is dangerous to handle and the instrumentation required to produce this signal is bulky. Another advantage of the present invention is that the $C^4D$ detection cell is isolated from the internal high voltage, environmental electrical noise and artifacts, which contributes to the lower detection limit of the system. As configured, the $C^4D$ detection cell of the present invention only requires external electrodes with adjustable distance integrated into shielded housing, therefore, it is user friendly and the cost is lowered.

It is understood that the foregoing description is given by way of illustration and that many variations may be made therein without departing from the embodiments described herein.

What is claimed is:

1. A portable electrophoretic capacitive coupled contactless conductivity detection ($C^4D$) system for electrophoresis analysis on a microfluidic chip having a channel defined by channel walls, the system comprising:
   (i) a housing, including a fluidic compartment having a chip stage for receiving the microfluidic chip;
   (ii) a cartridge detection cell releasably attached to the housing, releasable attachment of the cartridge cell to the housing causing electrical contact between the cartridge cell and the housing, the cartridge cell comprising:
   first and second emitting electrodes and
   first and second receiving electrodes; and
   wherein the first emitting electrode and the first receiving electrode are configured to be positioned adjacent to a first channel wall of said channel walls of the microfluidic chip, and
   the second emitting electrode and the second receiving electrode are configured to be positioned adjacent to a second channel wall of said channel walls of the microfluidic chip, the second channel wall being opposite the first channel wall;
   wherein the cartridge cell is releasably attached to an electronic circuit of the housing via a plurality of self latching connectors.

2. The detection system of claim 1, wherein the self latching connectors are selected from plugs and jacks or pins.

3. The detection system of claim 1, wherein the detection system is powered via a battery source.

4. The detection system of claim 3, wherein the battery source is selected from ±5 Volt or ±15 Volt batteries.

5. The detection system of claim 1, wherein the system is in communication with a computing device.

6. The detection system of claim 5, wherein the system is in wireless communication with the computing device.

7. The detection system of claim 1 in which the computing device is a laptop computer, personal digital assistant (PDA), a smart phone, or a portable meter.

8. The detection system of claim 1, wherein the system is handheld and includes an electronic compartment housing power components, battery components, an oscillator circuit and signal acquisition and processing components.

9. The detection system of claim 1 in which the cartridge cell comprises a first portion including the first emitting electrode and the first receiving electrode, and a second portion including the second emitting electrode and the second receiving electrode, the first and second portions of the cartridge cell being adapted for positioning to sandwich a microfluidic chip in the housing.

10. The detection system of claim 9 in which the upper and lower portions of the cartridge cell are hinged together.

11. The detection system of claim 9 in which, when the first and second portions of the cartridge cell are positioned to sandwich a microfluidic chip in the housing, the first and second emitting electrodes are aligned facing each other, and the first and second receiving electrodes are aligned facing each other.

12. The detection system of claim 1, further comprising:
a cover integrated on a surface of the housing and configured to secure the cartridge cell between the cover and the housing, and the cover being selected from a group consisting of: a pivotable cover and a detachable cover.

13. The detection system of claim 1 in which the cartridge cell further comprises; a ground plane located between the two emitting electrodes and the two receiving electrodes.

14. The detection system of claim 1 in which the cartridge cell further comprises:
a grounded metal housing; and
a Faraday cage surrounding the plurality of the detection electrodes inside the grounded metal housing;
wherein Faraday cage and the grounded metal housing shield the plurality of detection electrodes and the microfluidic chip from external fields.

15. The detection system of claim 1 wherein the plurality of detection electrodes are embedded in a polymer.

16. A capacitive coupled contactless conductivity detection ($C^4D$) cartridge cell for electrophoresis analysis on a microfluidic chip having a channel, the cell comprising:
a plurality of detection electrodes comprising two emitting electrodes and two
receiving electrodes, the two emitting electrodes being arranged for positioning adjacent to a first side of the microfluidic chip, and the two receiving electrodes being arranged for positioning adjacent to an opposite side of the microfluidic chip;
a detection area formed between the two emitting electrodes and two receiving electrodes located within the housing, the two emitting electrodes being arranged to be placed one on top and one at the bottom of the channel, and being configured to act as electrostatic images of each other and to transmit signals into the detection area, the receiving electrodes being arranged to be placed one on top and one at the bottom of the channel, and being configured to act as electrostatic images of each other and to receive the transmitted signals from the detection area; and
connection elements for releasably mechanically and electronically connecting the cartridge cell to a housing having an electronic circuit for supplying electrical signals to the cartridge cell and receiving signals from the receiving electrodes.

17. The cartridge cell of claim 16, wherein the connecting elements are sockets to receive pins, the sockets and pins cooperating as self latching connectors.

18. The cartridge cell of claim 16 further comprising;
a ground plane located between the two emitting electrodes and the two receiving electrodes.

19. The cartridge cell of claim 16 further comprising:
a grounded metal housing; and
a Faraday cage surrounding the plurality of the detection electrodes inside the grounded metal housing; and
wherein the Faraday cage and the grounded metal housing shield the plurality of detection electrodes and the microfluidic chip from external fields.

20. The cartridge cell of claim 16 wherein the plurality of electrodes are embedded in a polymer.

21. The cartridge cell of claim 16 in which the cartridge cell comprises a first portion including the first emitting electrode and the first receiving electrode, and a second portion including the second emitting electrode and the second receiving electrode, the first and second portions of the cartridge cell being adapted for positioning to sandwich a microfluidic chip in the housing.

22. The cartridge cell of claim 21 in which the upper and lower portions of the cartridge cell are hinged together.

23. The cartridge cell of claim 21 in which, when the first and second portions of the cartridge cell are positioned to sandwich a microfluidic chip in the housing, the first and second emitting electrodes are aligned facing each other, and the first and second receiving electrodes are aligned facing each other.

24. A portable electrophoretic contactless conductivity detection ($C^4D$) system comprising the cartridge cell of claim 16, and a housing for receiving the cartridge cell.

25. A portable electrophoretic contactless conductivity detection system comprising a plurality of cartridge cells of claim 16, and a housing for receiving any one of the cartridge cells, the plurality of cartridge cells having different dimensions.

* * * * *